United States Patent
Lamacchia

(10) Patent No.: US 10,893,692 B2
(45) Date of Patent: Jan. 19, 2021

(54) METHOD FOR THE DETOXIFICATION OF GLUTEN PROTEINS FROM CEREAL GRAINS AND USES THEREOF IN MEDICAL FIELD

(71) Applicant: NEW GLUTEN WORLD S.R.L., Foggia (IT)

(72) Inventor: Carmela Lamacchia, Foggia (IT)

(73) Assignee: NEW GLUTEN WORLD S.R.L, Foggia (IT)

( * ) Notice: Subject to any disclaimer, the term of this patent is extended or adjusted under 35 U.S.C. 154(b) by 138 days.

(21) Appl. No.: 16/062,543

(22) PCT Filed: Dec. 16, 2016

(86) PCT No.: PCT/EP2016/081589
§ 371 (c)(1),
(2) Date: Jun. 14, 2018

(87) PCT Pub. No.: WO2017/103214
PCT Pub. Date: Jun. 22, 2017

(65) Prior Publication Data
US 2019/0000118 A1 Jan. 3, 2019

(30) Foreign Application Priority Data
Dec. 17, 2015 (IT) .............................. UB2015A9442

(51) Int. Cl.
*A23L 5/20* (2016.01)
*A23L 3/3472* (2006.01)
(Continued)

(52) U.S. Cl.
CPC .............. *A23L 5/21* (2016.08); *A21D 13/066* (2013.01); *A23B 9/04* (2013.01); *A23L 3/3463* (2013.01);
(Continued)

(58) Field of Classification Search
CPC .......... A23L 33/00; A23L 5/34; A23L 3/3463; A23L 7/196; A23L 5/21; A23L 3/3472;
(Continued)

(56) References Cited

U.S. PATENT DOCUMENTS

| 2,011,050 A | 8/1935 | Newman |
| 2,240,442 A | 4/1941 | Paul |

(Continued)

FOREIGN PATENT DOCUMENTS

| CN | 101347195 A | 1/2009 |
| CN | 101623064 A | 1/2010 |

(Continued)

OTHER PUBLICATIONS

Catassi et al, "A Prospective, double-blind, placebo-controlled trial to establish a safe gluten threshold for patients with celiac disease" American Society for Nutrition; 85;160-6. 2007. 7 pages.
(Continued)

*Primary Examiner* — Subbalakshmi Prakash
(74) *Attorney, Agent, or Firm* — Steinfl + Bruno, LLP

(57) ABSTRACT

An improved method of detoxifying gluten proteins from cereal grains produces detoxified cereal grains with a reduction of antigenicity of toxic epitopes of gluten proteins by up to a range between 0 and 20 ppm. The detoxified cereal grains can be advantageously used for preparation of food products (e.g. bakery products, pasta or dairy products) having a manifest preventive and/or therapeutic effect for gut dysbiosis caused by bacterial or viral infective agents or by pathologies with a strong inflammatory or autoimmune component such as celiac disease, ulcerative colitis, Crohn's disease and irritable intestine syndrome.

13 Claims, 23 Drawing Sheets

(51) Int. Cl.
| | |
|---|---|
| A21D 13/066 | (2017.01) |
| A23L 5/30 | (2016.01) |
| A23L 7/10 | (2016.01) |
| A23L 7/196 | (2016.01) |
| A23L 3/3463 | (2006.01) |
| A23L 33/00 | (2016.01) |
| C12C 1/02 | (2006.01) |
| A23B 9/04 | (2006.01) |

(52) U.S. Cl.
CPC .............. *A23L 3/3472* (2013.01); *A23L 5/34* (2016.08); *A23L 7/196* (2016.08); *A23L 7/198* (2016.08); *A23L 33/00* (2016.08); *C12C 1/02* (2013.01); *A23V 2002/00* (2013.01)

(58) Field of Classification Search
CPC ......... A23L 7/198; A21D 13/066; C12C 1/02; A23B 9/04; A23V 2002/00
See application file for complete search history.

(56) References Cited

U.S. PATENT DOCUMENTS

| | | |
|---|---|---|
| 3,558,327 A | 1/1971 | Watkins et al. |
| 4,201,708 A | 5/1980 | Rao et al. |
| 4,778,690 A | 10/1988 | Sadel, Jr. et al. |
| 5,182,127 A | 1/1993 | Schwab et al. |
| 5,240,728 A | 8/1993 | Grenet et al. |
| 5,520,949 A | 5/1996 | Lewis et al. |
| 5,952,034 A | 9/1999 | Buchanan et al. |
| 8,753,701 B2 | 6/2014 | Jeong et al. |
| 2007/0292583 A1 | 12/2007 | Haynes et al. |
| 2011/0293724 A1 | 12/2011 | Hausch et al. |
| 2012/0255161 A1 | 10/2012 | Van Der Donck et al. |
| 2015/0272171 A1 | 10/2015 | Lamacchia et al. |

FOREIGN PATENT DOCUMENTS

| | | |
|---|---|---|
| KR | 20090042672 A | 4/2009 |
| WO | 01/54519 A1 | 8/2001 |
| WO | 2010/073283 A2 | 7/2010 |
| WO | 2014/053891 A1 | 4/2014 |

OTHER PUBLICATIONS

Final Office Action for U.S. Appl. No. 14/432,461, filed Mar. 30, 2015 on behalf of Universita Degli Studi Di Foggia, dated Feb. 15, 2019. 28 pages.
Guggenheim, J. "How Should Flour be Stored?" available at http://shelflifeadvice.com/content/how-should-flour-be-stored; accessed on Jun. 11, 2018; published on Jun. 18, 2009.
Lahdeaho et al, "Glutenase ALV003 Attenuates Gluten-Induced Mucosal Injury in Patients With Celiac Disease" AGA Institute, 146; 1649-1659. 2014. 10 pages.
Leffler, D. et al., "Kinetics of the Histological, Serologic and Symptomatic Responses to Gluten Challenge in Adults with Coeliac Disease", Gut, 62, pp. 996-1004, (2013),10 pages.
Non-Final Office Action for U.S. Appl. No. 14/432,461, filed Apr. 30, 2015 on behalf of Universita' Degli Studi Di Foggia, dated Jun. 12, 2018. 15 pages.
Pallai-Varasanyi, E. et al., "Selective Heating of Different Grain Parts of Wheat by Microwave Energy", In: Willert-Porada M. (eds) Advances in Microwave and Radio Frequency Processing, Springer, Berlin, Heidelberg, pp. 312-320, (2006). 9 pages.
Sarna, V. et al., "HLA-DQ-gluten tetramer blood gives better detection of coeliac patients Than biopsy after 14-day gluten challenge", Gut 2017 ; 0:1-8. 9 pages.
Arentz-Hansen, H. et al., "The Intestinal T-Cell Response to Alpha-Gliadin in Adult Celiac Disease is Focused on a Single Deaminated Glutamine Targeted by Tissue Trans-Glutaminase." *Journal of Experimental Medicine* 191 (4), pp. 603-612, (2000).
Brottveit, M., et al., "Mucosal Cytokine Response After Short-Term Gluten Challenge in Celiac Disease and Non-Celiac Gluten Sensitivity." *American Journal of Gastroenterology* 108, 842-850, (2013).
Burger, J.P.W., et al., "Systematic Review with Meta-Analysis: Dietary Adherence Influences Normalization of Health-Related Quality of Life in Coeliac Disease." *Clinical Nutrition* 36, 399-406, (2017).
Cenit, M.C., et al., "Intestinal Microbiota and Celiac Disease: Cause, Consequence or Co-Evolution?" *Nutrients* 7, 6900-6923, (2015).
Collado, M.C., et al., "Imbalances in Faecal and Duodenal *Bifidobacterium* Species Composition in Active and Non-Active Coeliac Disease." *BMC Microbiology* 8, p. 232, (2008). 9 pages.
Collado, M.C., et al., "Specific Duodenal and Faecal Bacterial Groups Associated with Paediatric Coeliac Disease." *Journal of Clinical Pathology* 62, 264-269, (2009). 7 pages.
Comino, I., et al., "Monitoring of Gluten-Free Diet Compliance in Celiac Patients by Assessment of Gliadin 33-mer Equivalent Epitopes in Feces." *American Journal of Clinical Nutrition* 95, 670-677, (2012).
Comino, I., et al., "Fecal Gluten Peptides Reveal Limitations of Serological Tests and Food Questionnaires for Monitoring Gluten-Free Diet in Celiac Disease Patients." *American Journal of Gastroenterology* 111, 1456-1465, (2016). 10 pages.
De Palma, G., et al., "Intestinal Dysbiosis and Reduced Immunoglobulin-Coated Bacteria Assoiated with Coeliac Disease in Children." *BMC Microbiology* 10, 63, (2010). 7 pages.
Di Cagno, R., et al., "Duodenal and Faecal Microbiota of Celiac Children: Molecular, Phenotype and Metabolome Characterization." *BMC Microbiology* 11, 219, (2011). 21 pages.
Fasano, A. et al. "Biological Perspectives: Physiological, Pathological, and Therapeutic Implications of Zonulin-Mediated Intestinal Barrier Modulation, Living Life on the Edge of the Wall." *The American Journal of Pathology* 173 (5), 1243-1252, (Nov. 2008).
Forsberg, G., et al., "Paradoxical Coexpression of Proinflammatory and Down-regulatory Cytokines in Intestinal T Cells in Childhood Celiac Disease." *Gastroenterology* 123 (3), 667-678, (2002).
Franks, A.H., et al., "Variations of Bacterial Populations in Human Feces Measured by Fluorescent in Situ Hybridization with Group-Specific 16S rRNA-Targeted Oligonucleotide Probes." *Applied and Environmental Microbiology* 64 (9), 3336-3345, (1998).
Gerrard, J.A., "Protein-Protein Crosslinking in Food: Methods, Consequences, Applications." *Trends in Food Science & Technology* 13, 391-399, (2002).
Gianfrani, C. et al. "Transamidation of Wheat Flour Inhibits the Response to Gliadin of Intestinal T Cells in Celiac Disease." *Gastroenterology* 133, 780-789, (2007).
Gianfrani, C., et al. "Microwave-based Treatments of Wheat Kernels do not Abolish Gluten Epitopes Implicated in Celiac Disease." *Food and Chemical Toxicology* 101, 105-113, (2017).
Guerrieri, N. et al., "Use of Spectroscopic and Fluorescence Techniques to Asses Heat-induced Molecular Modifications of Gluten," *Cereal Chemistry* 73 (3), 368-374, (1996).
Hosseini, E., et al., "Propionate as a health-promoting microbial metabolite in the human gut." *Nutrition Reviews* 69 (5), 245-258, (2011).
Klemenak, M., et al., "Administration of *Bifidobacterium breve* Decreases the Production of TNF-α in Children with Celiac Disease." *Digestive Diseases and Sciences* 60, 3386-3392, (2015).
Kokini, J.L., et al., "The Development of State Diagrams for Cereal Proteins." *Trends in Food Science and Technology* 5, 281-288, (1994).
Krishnan, H.B., et al., "Immunochemical Studies on the Role of the Golgi Complex in Protein-body Formation in Rice Seeds." *Planta* 169, 471-480, (1986).
Lahdeaho, ML., et al., "Small-Bowel Mucosal Changes and Antibody Responses After Low-and Moderate-Dose Gluten Challenge in Celiac Disease." *BMC Gastroenterology* 11, 129-137, (2011). 9 pages.
Lamacchia, C., et al., "Changes in Pasta Proteins Induced by Drying Cycles and Their Relationship to Cooking Behaviour." *Journal of Cereal Science* 46, 58-63, (2007).

(56) References Cited

OTHER PUBLICATIONS

Lamacchia, C., et al., "Changes in Durum Wheat Kernel and Pasta Proteins Induced by Toasting and Drying Processes." *Food Chemistry* 118, 191-198, (2010).
Lamacchia C., et al., "Changes in Wheat Kernel Proteins Induced by Microwave Treatment." *Food Chemistry* 197, 634-640, (Apr. 2016).
Landriscina, L., et al., "Impact of Gluten-Friendly™ Technology on Wheat Kernel Endosperm and Gluten Protein Structure in Seeds by Light and Electron Microscopy." *Food Chemistry* 221, 1258-1268, (2017). 11 pages.
Langendijk, P.S., et al., "Quantitative Fluorescence in Situ Hybridization of *Bifidobacterium* spp. With Genus-Specific 16S rRNA-Targeted Probes and Its Application in Fecal Samples." *Applied and Environmental Microbiology* 61 (8), 3069-3075, (1995).
Leffler, D.A., et al., "Kinetics of the Histological, Serologic and Symptomatic Responses to Gluten Challenge in Adults with Coeliac Disease." *Gut* 62(7), 996-1004, (2013). 22 pages.
Lending, C.R., et al., "Immunolocalization of Avenin and Globulin Storage Proteins in Developing Endosperm of *Avena sativa* L." *Planta* 178, 315-324, (1989).
Leszczynska, J., et al., "The Effect of Microwave Treatment on the Immunoreactivity of Gliadin and Wheat Flour." *European Food Research and Technology* 217, 387-391, (2003).
MacCaferri, S., et al., "In Vitro Fermentation of Potential Prebiotic Flours from Natural Sources: Impact on the Human Colonic Microbiota and Metabolome." *Molecular Nutrition and Food Research* 56, 1342-1352, (2012).
MacFarlane, G.T., et al., "Validation of a Three-Stage Compound Continuous Culture System for Investigation the Effect of Retention Time on the Ecology and Metabolism of Bacteria in the Human Colon." *Microbial Ecology* 35, 180-187, (1998).
Manz, W., et al., "Application of a Suite of 16S rRNA-Specific Oligonucleotide Probes Designed to Investigate Bacteria of the Phylum Cytophaga-Flavobacter-Bacteroides in the Natural Environment." *Microbiology* 142, 1097-1106, (1996).
Mazzeo, M.F., et al., "Biochemical Modifications of Gliadins Induced by Microbial Transglutaminase on Wheat Flour." *Biochimica et Biophysica Acta* 1830(11), 5166-5174, (2013).
Micard, V., et al., "Thermal Behavior of Native and Hydrophobized Wheat Gluten, Gliadin and Glutenin-Rich Fractions by Modulated DSC." *International Journal of Biological Macromolecules* 27, 229-236, (2000).
Miller, T.L., et al., "Pathways of Acetate, Propionate, and Butyrate Formation by the Human Fecal Microbial Flora." *Applied and Environmental Microbiology* 62 (5), 1589-1592, (1996).
Mitea, C., et al., "A Universal Approach to Eliminate Antigenic Properties of Alph-Gliadin Peptides in Celiac Disease." *PLoS One* 5 (12), 1-9, (Dec. 2010). 9 pages.
Mustalahti, K., et al., "Gluten-Free Diet and Quality of Life in Patients with Screen-Detected Celiac Disease." *Effective Clinical Practice* 5 (3), 105-113, (2002).
Nadal, I., et al., "Imbalance in the Composition of the Duodenal Microbiota of Children with Coeliac Disease." *Journal of Medical Microbiology* 56, 1669-1674, (2007).
Noel, T.R., et al., "The Glass-Transition Behaviour of Wheat Gluten Protens." *International Journal of Biological Macromolecules* 17 (2), 81-85, (1995).
Olivares, M., et al., "Double-Blind, Randomised, Placebo-Controlled Intervention Trial to Evaluate the Effects of *Bifidobacterium longum* CECT 7347 in Children with Newly Diagnosed Coeliac Disease." *British Journal of Nutrition* 112, 30-40, (2014).
Paavola, A., et al., "Gastrointestinal Symptoms and Quality of Life in Screen-Detected Celiac Disease." *Digestive and Liver Disease* 44, 814-818, (2012).
Rizzello, C.G., et al., "Highly Efficient Gluten Degradation by Lactobacilli and Fungal Proteases during Food Processing: New Perspectives for Celiac Disease." *Applied Environmental Microbiology* 73(14), 4499-4507, (2007).
Rossi, M., et al., "Editorial: Celiac Disease and Intestinal Bacteria: Not Only Gluten?" *Journal Leukocyte Biology* 87, 749-751, (2010).

Rubin, R., et al., "Evidence for the Presence of Two Different Types of Protein Bodies in Wheat Endosperm." *Plant Physiology* 99, 718-724, (1992).
Sanchez, E., et al., "Duodenal-Mucosal Bacteria Associated with Celiac Disease in Children." *Applied and Environmental Microbiology* 79 (18), 5472-5479, (2013).
Sanz, Y., et al., "Differences in Faecal Bacterial Communities in Coeliac and Healthy Children as Detected by PCR and Denaturing Gradient Gel Electrophoresis." *FEMS Immunology and Medical Microbiology* 51, 562-568, (2007).
Sarna, V., et al., "HLA-DQ—Gluten Tetramer Blood Test Accurately Identifies Patients With and Without Celiac Disease in Absence of Gluten Consumption." *Gastroenterology* 154, 886-896, (2018). 17 pages.
Schippa, S., et al., "A Distinctive 'Microbial Signature' in Celiac Pediatric Patients." *BMC Microbiology* 10, 175, (2010). 10 pages.
Schofield, J.D., et al., "The Effect of Heat on Wheat Gluten and the Involvement of Sulphydryl-Disulphide Interchange Reactions." *Journal of Cereal Science.1*, 241-253, (1983).
Schuppan, D., et al., "Reviews in Basic and Clinical Gastroenterology; Celiac Disease: From Pathogenesis to Novel Therapies." *Gastroenterology* 137, 1912-1933, (2009).
Schuppan, D., et al., "Celiac Disease: From Pathogenesis to Novel Therapies." *Gastroenterology* 137, 1912-1933, (2009).
Singh, H., et al., "Changes in Proteins Induced by Heating Gluten Dispersions at High Temperature." *Journal of Cereal Science* 39, 297-301, (2004).
Smecuol, E., et. al., "Exploratory, Randomized, Double-blind, Placebo-controlled Study on the Effects of *Bifidobacterium infantis* Natren Life Start Strain Super Strain in Active Celiac Disease." *Journal of Clinical Gastroenterology* 47, 139-147, (2013).
Stoven, S., et al., "Advances in Translational Science, Celiac Disease: Advances in Treatment via Gluten Modification." *Clinical Gastroenterology and Hepatology* 10 (8), 859-862, (2012).
Tejero-Sarinena, S., et al., "In vitro Evaluation of the Antimicrobial Activity of a Range of Probiotics Against Pathogens: Evidence for the Effects of Organic Acids." *Anaerobe* 18, 530-538 (2012).
Tilley, K.A., et al., "Tyrosine Cross-Links: Molecular Basis of Gluten Structure and Function." *Journal of Agricultural and Food Chemistry* 49, 2627-2632, (2001).
Tosi, P., et al., "Trafficking of Storage Proteins in Developing Grain of Wheat." *Journal of Experimental Botany* 60 (3), 979-991, (2009).
Tosi, P., et al., "Distribution of Gluten Proteins in Bread Wheat (*Triticum aestivum*) Grain." *Annals of Botany* 108, 23-35, (2011).
Valdés, I., et al., "Innovative Approach to Low-Level Gluten Determination in Foods Using a Novel Sandwich Enzyme-Linked Immunosorbent Assay Protocol." *European Journal of Gastroenterology & Hepatology* 15 (5), 465-474, (2003).
Vert, M., et al., "Terminology for Biorelated Polymers and Applications (IUPAC Recommendations 2012)." *Pure and Applied Chemistry* 84 (2), 377-410, (2012).
Wacklin, P., et al., "The Duodenal Microbiota Composition of Adult Celiac Disease Patients Is Associated with the Clinical Manifestation of the Disease." *Inflammatory Bowel Disease* 19 (5), 934-941, (2013).
Wacklin, P., et al., "Altered Duodenal Microbiota Composition in Celiac Disease Patents Suffering From Persistent Symptoms on a Long-Term Gluten-Free Diet." *American Journal of Gastroenterology* 109, 1933-1941, (2014). 9 pages.
Weegels, P.L., et al., "Effects on Gluten of Heating at Different Moisture Contents. I. Changes in Functional Properties," *Journal of Cereal Science* 19, 31-38, (1994).
Definitions of "Denature" from http://www.dictionary.com/browse/denature; accessed on Nov. 17, 2017. 4 pages.
Definition of "Room Temperature." (2011). In *The Editors of the American Heritage Dictionaries* (Ed.), *The American Heritage dictionary of the English language*. (5th ed.). [Online]. Boston: Houghton Mifflin. Available from: http://search.credoreference.com/content/entry/hmdictenglang/room_temperature/O [Accessed May 29, 2017].
International Search Report for Application No. PCT/EP2016/081589 filed on Dec. 16, 2016 on behalf of New Gluten World S.R.L, dated Feb. 16, 2017. 4 pages.

(56) References Cited

OTHER PUBLICATIONS

Written Opinion for Application No. PCT/EP2016/081589 filed on Dec. 16, 2016 on behalf of New Gluten World S.R.L, dated Feb. 16, 2017. 6 pages.
International Preliminary Report on Patentability for Application No. PCT/EP2016/081589 filed on Dec. 16, 2016 on behalf of New Gluten World S.R.L, dated Dec. 7, 2017. 12 pages.
International Search Report for Application No. PCT/1132013/000797 filed on Apr. 29, 2013 on behalf of Universita' Degli Studi Di Foggia, dated Sep. 3, 2013. 4 pages.
Written Opinion for Application No. PCT/IB2013/000797 filed on Apr. 29, 2013 on behalf Universita' Degli Studi Di Foggia, dated Sep. 3, 2013. 5 pages.
Restriction Requirement for U.S. Appl. No. 14/432,461, filed Mar. 30, 2015 on behalf of Universita' Degli Studi Di Foggia, dated Jan. 26, 2017. 8 pages.
Non-Final Office Action for U.S. Appl. No. 14/432,461, filed Mar. 30, 2015 on behalf of Universita' Degli Studi Di Foggia, dated May 31, 2017. 17 pages.
Final Office Action for U.S. Appl. No. 14/432,461, filed Mar. 30, 2015 on behalf of Universita' Degli Studi Di Foggia, dated Nov. 24, 2017. 33 pages.
EPO Communication pursuant to Article 94(3) EPC for European Application No. 13731862.2, dated Apr. 22, 2016. 6 pages.
EPO Communication pursuant to Article 114(2) EPC for European Application No. 13731862.2, dated Feb. 18, 2016. 9 pages.
Acknowledgement of receipt of observations by third parties (Article 115 EPC) for European Application No. 13731862.2, dated Feb. 18, 2016. 1 page.
Response to Official Communication pursuant to Article 94(3) with Annex containing Inventor's statements, dated Aug. 1, 2016. 21 pages.
AACC International. Approved Methods of Analysis, 11th Ed. Method 38-12.02. Wet Gluten, Dry Gluten, Water-Binding Capacity and Gluten Index. Approved Nov. 2000. *AACC International*, St. Paul, MN, U.S.A. http://dx.doi.org/10.1094/AACCIntMethod-38-12.02. 1 page.
ICC. "Determination of Wet Gluten Quantity and Quality (Gluten Index ac. to Perten) of Whole Wheat Meal and Wheat Flour (*Triticum aestivum*)" Approved in 1994. *International Association for Cereal Science and Technology*. 1 page.
Gliadin 23. May. 2016, 16:08:11, Spline, Ser.No: 13598.194, Version: 1.94. Report of data obtained in Experiments 1, 2, and 3 contained in NPL-01. 3 pages.
Gliadin 10. Jun. 2016, 17:04:01, Spline, Ser.No: 13598.194, Version: 1.94 Report of data obtained in Experiments 1, 2, and 3 contained in NPL-01. 3 pages.
WikiHow "How to Cook Wheat Berries" Internet Archive May 31, 2011. Downloaded Mar. 3, 2017. 2 pages.
Non-Final Office Action for U.S. Appl. No. 14/432,461, filed Apr. 30, 2015 on behalf of Universita' Degli Studi Di Foggia, dated Mar. 4, 2020. 29 Pages.

METHOD FOR THE DETOXIFICATION OF GLUTEN PROTEINS FROM CEREAL GRAINS AND USES THEREOF IN MEDICAL FIELD

CROSS-REFERENCE TO RELATED APPLICATIONS

The present application is the U.S. National Stage of International Patent Application No. PCT/EP2016/081589 filed on Dec. 16, 2016 which, in turn, claims priority to Italian Patent Application No. UB2015A009442 filed on Dec. 17, 2015.

The present invention relates to an improved method for detoxifying gluten proteins from cereal grains which makes it possible to obtain detoxified flours with a reduction of the antigenicity of the toxic epitopes of the gluten proteins down to a range between 0 and 20 ppm and such that they can be advantageously used for the preparation of food products (e.g. bakery products, pasta or dairy products) having a manifest preventive and/or therapeutic effect for gut dysbiosis caused by bacterial or viral infective agents or by pathologies with a strong inflammatory or autoimmune component such as celiac disease, ulcerative colitis, Crohn's disease and irritable intestine syndrome.

Gluten is a food complex consisting mainly of proteins. Prolamins constitute approximately 80% of the entire protein fraction present in cereal caryopsis and are classified on the basis of their solubility in hydroalcoholic solution in gliadin and glutenins. Gliadins, soluble in hydroalcoholic solutions, are monomeric molecules typically classified as alpha, beta, gamma and omega (according to electrophoretic mobility) for which the monomeric condition is due to the absence of cysteine residues, as in the case of omega-gliadins, or to the presence of only intramolecular disulfide bonds (the remaining gliadins).

Glutenins, instead, are a polymeric complex, insoluble in hydroalcoholic solutions constituted by sub-units with high (HMW-GS) and with low (LMW-GS) molecular weight, stabilized by intermolecular disulfide bridges.

Gliadins and glutenins provide flours with the technological properties; gliadins contribute to the viscosity of the dough, while glutenins are responsible for its elasticity and tenacity.

In particular, the quantity and the dimensions of the glutenin polymers are positively correlated with the technological properties of the doughs.

Therefore, these characteristics of glutenin polymers depend on the ability of the individual component sub-units to form more or less extended polymers.

Gluten, in particular, is not present as such in cereal caryopsis, but is formed at a later time; gluten as a protein complex is formed following hydration and the mechanical action of kneading and it is an essential element for the processing of flours and for bread-making, inasmuch as it provides viscosity and elasticity to the dough.

As is well known, when water is added to flour, gliadins (formed by a single protein chain) start to hydrate forming fibrils (small, thin fibers) that provide extensibility to the gluten mesh. Simultaneously, glutenins (comprising several protein sub-units) are also assembled, originating a mesh and forming a stable, highly cohesive structure, which provides the dough with consistency and a certain resistance to extension and elasticity.

The strength and the degree of leavening thus depends on the proportion between the gliadin and glutenin content of the flour. The ratio between the two classes of proteins depends on the variety of cereal considered and provides the gluten with the ability to deform and to withstand stretching.

During the mechanical kneading action, the gliadin fibrils and the glutenin polymers start to entwine with each other, forming a three-dimensional mesh that incorporates starch granules, lipids, mineral salts, water and air bubbles, the latter being very important for the alcoholic fermentation of the yeasts that are then added and that, through the production of alcohol and carbon dioxide, determine the expansion of the meshes of the gluten, which expand and stretch making the volume of the dough increase. The subsequent cooking determines the denaturing/coagulation of the proteins and so the gluten, losing its ability to stretch, irreversibly stabilizes the structure and the shape of the dough.

As a protein complex, gluten has no particular nutritional properties, because it is poor in essential amino acids such as lysine, methionine and tryptophan.

The absence of this compound in the diet entails no specific nutritional risk.

On the other hand, gluten is capable of performing toxic activity, in particular with respect to the intestinal mucosa; permanent intolerance to wheat gluten and to the corresponding proteins of rye, barley and oat, such as to trigger the inflammatory cascade of the cytodamaging cytokines, is defined as celiac disease.

Initially, the toxic action of gluten was thought to be caused by the alpha fraction of gliadin; subsequently, it was demonstrated that omega gliadins and glutenins are also able to cause damage to the intestinal mucosa, as are the prolamins of similar cereals such as barley (hordein), rye (secalin) and oat (avenin).

Of recent interest has been the study of a peptide of 33 amino acids of alpha-gliadins known as 33-mer; said peptide is able to withstand the proteolytic action of the digestive enzymes, arriving whole at the intestinal mucosa where, having a high affinity for tissue transglutaminase, it exercises a powerful immunogenic action in sensitive individuals; this action would be determined, as a result of the deamidation of the toxic epitopes of the peptide, by an intense activation of the CD4 T lymphocytes that release cytodamaging inflammatory cytokines (Shuppan D. et al., 2009).

It has also been demonstrated that other toxic epitopes of alpha-gliadin are apparently able to induce apoptosis of enterocytes originating from explants of intestinal mucosa of celiac patients.

Hence, gluten has a harmful effect on the intestinal mucosa both by triggering the inflammatory cascade of cytokines, and causing a direct toxic effect.

Approximately 30% of the general population bears celiac disease susceptibility genes, HLA-DQ2/8; however, only 2-5% of these individuals will actually develop celiac disease, which suggests that additional environmental factors contribute to the development of the disease (Rossi M. et al., 2010). The additional factors that influence the development of celiac disease are unknown, but they could include alteration in the intestinal microbiota. In fact, some studies have shown that patients ongoing celiac disease had an altered quali-quantitative composition of the fecal and duodenal microbiota compared to healthy individual, subsequently partially restored after treatment with a gluten-free diet. In particular, the most important changes pertained to variations in quantity of Firmicutes and Proteobacteria in children and adults with active celiac disease (Sanchez E. et al., 2013; Wacklin P. et al., 2013). Other studies have reported a decrease in the concentration of protective bacteria with anti-inflammatory effects, such as *Bifidobacte-*

*rium*, and increase in Gram-negative bacteria, such as *Bacteroides* and *Escherichia coli* in patients with active celiac disease (Collado M. et al., 2009; Collado M. et al., 2008; Di Cagno R. et al., 2011).

Moreover, children affected by celiac disease generally exhibit an increase in *Staphylococcus* spp. (Collado M. et al., 2009; Collado M. et al., 2008; Di Cagno R. et al., 2011, *Clostridium* spp (Di Cagno R. et al., 2011; De Palma G. et al., 2010) and a decrease in *Lactobacillus* spp (Di Cagno R. et al., 2011, Sanz Y. et al 2007; Nadal M. et al., 2007). In addition, patients with celiac disease exhibited an altered composition and metabolic function of the microbiota in terms of production of short chain fatty acids (SCFA) (Di Cagno R. et al., 2011; Schippa S. et al., 2010). A study has demonstrated that the intestinal microbial composition in patients affected by celiac disease was associated with the clinical manifestation of the disease. The intestinal flora in patients in the presence of gastrointestinal symptoms is dominated by Proteobacteria, while the microbiota of patients with Dermatitis Herpetiformis or of individuals who live in dyspepsia (controls) have seen the prevalence of Firmicutes (Wacklin P. et al., 2013).

To date, the sole treatment for celiac patients is the complete exclusion of gluten from the diet. A so-called "gluten-free" diet alleviates many of the symptoms, but surprisingly studies suggest that such a treatment does not allow fully to restore the profiles of the microbiota present in healthy subjects (Wacklin P. et al., 2014).

It seems that the diet itself prevents complete restoration according to the normal microbial models. In healthy patients subjected to a gluten-free diet, too, the delicate balance between gram-positives and gram-negatives fails, with the useful bacteria rapidly replaced by opportunist pathogens. The long-term outcome can lead to a weakening of the immune defenses and to a state of chronic inflammation. This engenders a situation in which celiac patients, while adhering to a rigorous gluten-free diet, are still exposed to the risk of inflammation and infections, and potentially could suffer from rather unpleasant symptoms as well as an increase in health risks.

The potential use of probiotics in the management of the celiac disease is supported by gut dysbiosis generally associated to celiac disease and to the role attributed to these potentially beneficially beneficial bacteria (i.e., "probiotics") in keeping the intestinal barrier functioning and regulating the innate, adaptive response of the immune system. FIG. 1 shows a model that illustrates the pathogenesis of celiac disease. The specific genetic makeup of the host and environmental factors could promote the colonization of pathobiont and reduce symbionts, thereby determining dysbiosis. Dysbiosis can contribute to interrupt the homeostasis and the immune integrity of the intestine, thus promoting the insurgence of celiac disease and aggravating pathogenesis (Cenit M. C. et al., 2015).

Based on this hypothesis, to date three studies have been carried out on as many interventions on celiac patients selected at random, controlled with placebos in a double-blind procedure. In one of these interventions, *Bifidobacterium infantis* NLS was administered to untreated celiac patients to assess the effect of the probiotic independently of the gluten-free diet. This study has shown an improvement in some gastrointestinal symptoms, specifically indigestion and constipation, in untreated patients with celiac disease after the administration of *Bifidobacterium infantis* NLS. In addition, it did not improve the situation of diarrhea or of abdominal pains, or modified intestinal permeability or the pro-inflammatory state measured as in the serum levels of some cytokines and chemokines (Smecuol E. et al., 2013). Another study on interventions analyzed the influence of *Bifidobacterium longum* CECT 7347 in celiac children with a gluten-free diet, in order to assess whether these probiotic bifid bacteria could improve the effectiveness of the gluten-free diet. This study revealed a decrease in CD3+ peripheral T lymphocytes and a tendency to the reduction of the serum levels of TNF-α after the administration of *Bifidobacterium longum* CECT 7347 and also a significant reduction in the number of *Bacteroides fragilis* and sIgA in feces compared to the group treated with placebo (Olivares M. et al., 2014). A recent three-month long study evaluated the effect of the combination of the strains *Bifidobacterium breve* BR03 and *Bifidobacterium breve* B632, compared to the placebo, in children with celiac disease with a gluten-free diet. The study reported that strains of *Bifidobacterium breve* reduce the production of pro-inflammatory TNF-α cytokines in children with celiac disease with a gluten-free diet (Klemenak M. et al., 2015).

Limitations in the use of probiotics as a therapy in the prevention and care for celiac disease reside in the fact that they are microorganisms that must reach the intestine alive and that must adhere to intestinal cells. Moreover, probiotics are exogenous microorganisms whose colonization could be transient and the modest results of the probiotics obtained in the aforementioned studies can also be explained by the relatively low number of bacteria present in commercial preparations also by the fact that individual species may not be able to compete with the intestinal flora comprising myriads of bacteria belonging to over 40,000 different species.

From this need—i.e. the need to be able to produce food products that are typical of the Mediterranean diet, such as bread and past derived from wheat in which the gluten present is not only not immunogenic, but is actually able to strengthen the intestinal microflora of the celiac patient serving as a protective agent with respect to the useful microorganisms until the balance of the microbiota is restored, which can be used in the prevention and in the dietetic therapy of celiac disease, caused by loss of the homeostasis generated by a weak useful microflora—stems this invention.

The international patent application WO2014/053891 describes a method for the detoxification of gluten proteins from grains of cereals to make them non-immunogenic for celiac patients and to reduce the antigenicity of the toxic epitopes to a range between 60 and 40 ppm (Lamacchia C. et al., 2016).

The author of the present invention has devised an improved method for detoxifying gluten proteins from cereal grains directed at obtaining flours that are not only detoxified, but flours in which the antigenicity of the proteins is further reduced down to a range between 0 and 20 ppm, and with therapeutic effect in the prevention and in the therapeutic treatment of gut dysbiosis caused by a weak useful microflora as a result of inflammation and/or infection in a far broader range of patients. In particular, the author of the present invention has identified a state of vitreous transition that gluten proteins are able to reach by means of a specific alternation of steps of the method for processing the grains hydrated before milling according to the present invention: rapid microwave heating and evaporation of the free and bonded water contained in the grains.

More specifically, through the alternation of the steps of rapid microwave heating and of slow evaporation of the water contained in the grains, it is possible to solve the problem of the production of flours with gluten that—in addition to not being immunogenic and toxic for celiac patients—exhibits a reduction of the antigenicity of the toxic epitopes of gluten to a range between 0 and 20 ppm and is able to strengthen, in a surprising and unexpected way, the useful intestinal microflora of the same celiac patient, restoring its balance and preventing the insurgence and/or the perpetuation of the intestinal inflammation present also in numerous other chronic conditions.

Hence through the method of the present invention it is possible to produce different food products (i.e. bread-making or bakery products or pasta), which can be used in the prevention and in the dietetic therapy of chronic intestinal inflammatory pathologies such as celiac disease, ulcerative colitis, Crohn's disease, irritable bowel syndrome caused by loss of the homeostasis generated by a weak probiotic microflora.

Therefore, the present invention relates to a method for the detoxification of gluten from grains of cereals, comprising the following steps:

a) hydrating the cereal grains with water up to a humidity degree of the grains comprised between 15 and 18%;

b) treating the hydrated grains by electromagnetic waves, preferably microwaves or infrared, for a time and with a power necessary to reach a temperature of the grains comprised between 60 and 70° C.;

c) suspending the irradiation until a temperature comprised between 50 and 60° C. is reached and simultaneous water evaporation with a humidity loss of the grains comprised between 14 and 16% in comparison to step a);

d) treating the hydrated grains by electromagnetic waves, preferably microwaves or infrared, for a time and with a power necessary to reach a temperature of the grains comprised between 80 and 90° C.;

e) suspending the irradiation until a temperature comprised between 70 and 80° C. and simultaneous water evaporation with a humidity loss of the grains comprised between 40 and 44% in comparison to step a);

f) treating the hydrated grains by electromagnetic waves, preferably microwaves or infrared, for a time and with a power necessary to reach a temperature of the grains comprised between 110 and 120° C.;

g) suspending the irradiation inside the microwave oven until a temperature comprised between 80 and 90° C. and simultaneous water evaporation with a humidity loss of the grains comprised between 50 and 60% in comparison to step a);

h) slow cooling of the detoxified grains at room temperature.

The aforementioned method is preferably carried out using microwaves, more specifically using a microwave oven as a device for emitting said microwaves in the different steps of processing of the hydrated grains.

Alternatively, a laser device can be used for emitting the electromagnetic waves.

According to a preferred embodiment, the method according to the invention comprises an additional step i) of milling the grain of step h) to obtain the flour or the semolina. According to an alternative embodiment, the method according to the present invention comprises an additional step l) of extracting with solvent (i.e. water/saline solution of sodium chloride) from the flours or semolina of step i) to obtain the detoxified gluten.

The term "ambient temperature" preferably means a temperature range between 20° C. and 25° C.

Preferably, the grains are cereal, more preferably wheat, barley, rye or oat.

In steps b), d), f) of the method according to the invention, what is important is the temperature reached inside the grains, not the power of the electromagnetic waves that, through the water contained in the grains, allow to reach high temperatures in a short time.

The images shown in FIG. 2 demonstrate that the microwaves themselves do not determine the change in the structure of the gluten protein, but rather the attainment of given temperatures and humidity conditions in particular in the last step of suspending the irradiation-evaporation of the water (step g) of the process) in which the humidity content of the grains reached 5-7% and temperature attains approximately 100° C. From FIG. 2 it is also readily apparent that, in this step only, gluten proteins are no longer totally recognizable from the fluorescent antibodies within the grains.

All steps described above are necessary: hydrating the grains to a humidity between 15 and 18% of step a) enables the seed to accumulate the quantity of water necessary to transform the electromagnetic waves, preferably microwaves, into thermal energy in a thermalization process.

Water molecules can rotate, vibrate and align under the action of the electric fields. In their movement, they collide with the neighboring molecules and this kind of molecular rubbing causes heating of the irradiated mass.

The subsequent irradiation of step b) with microwaves enables heating the sample which in the first step of irradiation must reach a temperature between 60 and 70° C. The higher the degree of humidity, the lower will the power applied in a certain time interval to reach the desired temperature have to be. The time interval to reach the desired temperature will be a function of the mass to be irradiated.

By way of example: 100 g of grains with humidity of 15-18% will reach the temperature of 60-70° C. in 1 minute applying a power of 750 Watt.

Hence, while the degree of humidity is inversely correlated to the power to be applied, the irradiation time is directly proportional to the mass of the sample to be irradiated.

The step of suspending irradiation-evaporation must be carried out preferably within the microwave oven to allow a process of transferring the water from the innermost layer of the grains to the periphery and from the periphery to the surface and from the surface of the grains to the outside environment. The process has to take place slowly and not exposing the grains to the external temperature of the device that is used for heating, i.e. the microwave oven. This could cause only an evaporation of the water on the surface of the grains, not allowing the elimination of a part of the water bonded to the molecules.

The step of irradiating and suspending irradiation-evaporation are repeated n times, alternately, until the attainment of the state of vitreous transition of gluten proteins, i.e. the state in which, in determined conditions of humidity and temperatures, gluten proteins become plastic (see FIG. 3).

Each protein has its own conformation, i.e. a characteristic three-dimensional shape, in which different levels of organization can be identified. As shown, the primary structure is given by the sequence of amino acids in the polypeptide chain, mutually joined by covalent bonds. The next level is the secondary structure, which is formed when hydrogen bonds are established between the amino acids of the primary structure, causing its torsion. The tertiary structure of a protein is produced by the interaction between amino acids located in different points of the secondary structure and it is mostly due to the folds of the polypeptide chain in the junction segments between the alpha helices and the folded sheets of the secondary structure. The quaternary structure is the result of the way in which two or polypeptide chains, called sub-units, bind together and interact with each other. The method of the present invention enables gluten proteins to reach a state of vitreous transition in which the molecules do not vibrate, but move thanks to the breaking of the bonds of the secondary and tertiary structure and the molecules become plastic/rubbery (Noel T. R. et al., 1995; Micard V. and Guilbert S., 2000).

In particular, the hydrogen bonds and the ionic bonds that bind groups with opposite charge, but also the disulfide bonds that enable the proteins to maintain their secondary and tertiary conformation, break enabling molecules to move in space, modifying their secondary and tertiary structure.

The gluten protein made plastic by this process will tend to aggregate in a non-conventional manner, because they are present in native form in protein bodies of the mature grains (Tosi P. et al., 2011) as shown in FIG. 4. FIG. 4 shows that after the treatment with the method of the invention, not only are the proteins not recognizable from their own antibodies, but an aggregation of the proteins themselves in the protein body of the treated seeds with respect to the control seeds is evident. In particular, the proteins will not aggregate by means of covalent bonds (FIG. 5), as occurs in a structure of the gluten already formed and subjected to high temperatures (cooking the dough in the oven, drying the pasta; Lamacchia C. et al., 2007; Gerrard J. A., 2000), but by means of ionic bonds that join groups with opposite charge generated by the change of the secondary and tertiary structure of the molecule when present in native form in the protein bodies of the mature grains. FIG. 5 shows a gel electrophoresis conducted in reducing conditions that does not show any differences in the molecular weights of the proteins extracted from the flours of the control seeds and seeds treated with the method of the present invention, highlighting that the protein not only do not undergo changes in the primary structure, but also that the visible aggregation in the protein bodies of the seeds after heat treatment according to the method of the present invention cannot be through covalent, dityrosine and/or isopeptide bond (Gerrard J. A., 2000; Lamacchia C. et al., 2007; Tilley K. A. et al., 2001). In this case, a shift of the protein bands towards higher molecular weights should have been observed.

Therefore, the aggregation observed in the protein bodies of the treated seeds, cannot be covalent, i.e. is not attained through the formation of covalent bonds.

Step h) of slow cooling at ambient temperature of the method according to the invention enables the molecules to crystallize in this state of non-conventional aggregation.

The key points of this improved method are represented by:

1) use of water, which serves a dual function. The first one is to transform the electromagnetic waves, preferably the microwaves, into thermal energy in a thermalization process. The second one is to enable gluten proteins to reach a state of vitreous transition, a state that makes them plastic, evaporating slowly and dragging with them a part of the bonded water as well.

Use of microwaves is particularly preferred, because since they are not ionizing radiations they are not able to break bonds. Hence, their sole function is to allow the water molecules to vibrate and to generate heat in a short time.

3) generation of the heat, which also has a dual function. It enables free and bonded water to evaporate, and to gluten proteins, enclosed in the protein bodies of the mature grains in native form, to reach a state in which the proteins do not vibrate, but move.

This movement is enabled by the breaking of hydrogen bridges and ionic bonds that cause the secondary and tertiary structure of the proteins themselves to change, making them plastic (FIG. 3). This change manifestly leads to an exposure of charges by the protein, justified by the fact that gluten with this process becomes soluble in water. The exposure of the charges due to a loss of the secondary and tertiary structure of the proteins leads to an aggregation between the proteins present in the same protein body and with different charge. FIG. 6 schematically shows the case in which before the application of the method of the present invention the gluten proteins are enclosed in protein bodies of the wheat grains assuming their native three-dimensional structure. After the application of the method of the present invention, the proteins reach the state of vitreous transition, become plastic losing their three-dimensional structure. This change leads to an exposure of charges by the protein, justified by the fact that gluten, with this process, become soluble in water. The exposure of the charges due to a loss of the secondary and tertiary structure of the proteins leads to an aggregation between the proteins present in the same protein body and with different charge. One could hypothesize gliadin (−)+LMW (+), albumin (+)+gliadin (−), globulin (+)+gliadin (−), as shown in the image depicted in FIG. 6.

To further confirm the above hypothesis, further to the immunofluorescence analysis of the six steps A-F of the detoxification process in panel a) of FIG. 21, panel b) shows the image thresholding analysis of the above steps by using 'Image J' software (http://imagej.nih.gov/ij). Panel c) shows the results of the SDS-PAGE of gliadin protein fractions relative to each step and of the control weight flour (CWF) extracted in 70% EtOH. Panel d) shows a summarizing table of the % decrease relative to the values of MGV (Mean Grey Value) obtained from the analysis of microscopy image steps and optical density (OD) relative to SDS-PAGE expressed gliadin protein fractions. From the image analysis of the six steps A-F illustrated in panel b) it is possible to observe by naked eye a regular decrease of brightness, that is the fluorescence due to marking by 0610 antibody, which recognize the gliadin protein fraction and LMW-GS, in each step. The decrease is confirmed by the analysis of the Mean Grey Values reported in the table illustrated in panel c), wherein a comparison between each step has been carried out. The regular and meaningful decrease in each step is representative of as structural change of the proteins, which is no more recognized by antibodies. Decrease is regular because at each step corresponds a temperature and humidity value, at which a precise protein class stats its structural change, that is its "transition" from solid to gummy/plastic state. In other words, each protein class will present its own relative vitreous transition temperature (Tg) based on its chemical structure, beyond that the polymer chains will be free to move and to modify the conformation. Particularly, at lower temperatures (between 50-65° C.), thus in the starting steps of the process, albumins, globulins and LMW proteins will be the first to encounter a change together with HMWs (as observed by Lamacchia C. et al., 2007); at temperature of about 70° C. gliadins will start first to change their structural conformation and will end at the final steps of the process (80-90° C.). In order to demonstrate this event, an SDS-PAGE analysis of ethanol extracted gliadins from the grains in any step process has been carried out. The SDS-PAGE analysis shows in particular a band decrease in steps A to F and with respect to the control, showing how gliadins, that do not present cysteine residues available to create inter chains disulphide bonds in their natural conformation, are involved in this type of bond during the intermediate and final steps of the process due to a conformational change which causes an exposure of cysteine residues.

It is possible to observe that the band reduction (OD) is not comparable to the brightness reduction (MGV) observed during the six steps of the process by microscopy technique, thus confirming that the cross-reactivity reduction of the gluten proteins against 0610 antibody is due to a conformational change of the proteins and/or by epitope coverage, which is caused by a strong aggregation between the proteins during the process steps (as shown in FIG. 4), generated by ionic bonds connecting opposite charge groups occurring after the change of tertiary structure following vitreous transicion and not by covalent bonds (see FIGS. 5 and 21).

4) by slow cooling, which allows the new protein structure to remain crystallized in this new state.

The present invention also relates to detoxified grains, flour or semolina or gluten obtainable with the method according to the invention. The flour or the semolina can be wheat, rye, barley or oat and they are obtainable after the milling of the additional step i). Gluten can be wheat, rye, barley or oat, obtainable after extraction with solvent from the flours and/or from the semolina of the additional step 1).

The term "detoxified" in the context of the present invention when referred to flours or semolina, means a level of toxic gluten epitopes reduced to a range between 0 and 20 ppm. This makes it possible to consider these flours or semolina to be "gluten free" for all purposes of the law, although gluten is still present within them.

The invention relates to a food product comprising wheat flour, wheat semolina, barley or oat, selected between bread, pasta, bakery products, breakfast cereals and beer.

Alternatively, the invention relates to dairy products (i.e. yoghurt, ice cream, fermented milk, cheese, mozzarella, butter, cream, ricotta) to which can be added the detoxified gluten obtained according to step 1) of the method of the invention.

In particular, the detoxified gluten obtained according to step 1) of the method of the invention can advantageously be used as a thickening agent for the preparation of food products, not only dairy, but also in other categories of products such as cold cuts, ice cream, baby foods, sauce and juice. Therefore, such food products are also included in the scope of protection of the present invention inasmuch as they are intended for those populations of individuals for whom a gluten free or low lactose diet.

Briefly, a first advantage is that from the semolina and from the flours produced in accordance with the method of the invention it will be possible to produce foods for celiac patients with antigenicity of the toxic gluten epitopes reduced between 0 and 20 ppm, with organoleptic characteristics that are equivalent in taste and appearance to those commonly used in the Mediterranean diet, but also therapeutic with respect to the intestinal microflora of the celiac patient, restoring its balance, and protecting it and strengthening the useful microflora.

Therefore, the present invention further relates to the detoxified grains, flour, semolina or gluten or a food product based on one of them or supplemented with one of them for use in medical field for the prevention or the treatment of gut dysbiosis.

A second advantage is that from the grains, from the semolina, from the flours, or from the gluten thus produced, it will be possible to produce foods for the dietetic therapy of all those pathologies in which the alteration of the intestinal microbiota increases the risk to develop a susceptibility to chronic intestinal diseases of an inflammatory and/or autoimmune nature, selected, by way of non-comprehensive example, from the group that consists of celiac disease, ulcerative colitis, Crohn's disease, and intestine syndrome, as well as systemic metabolic diseases such as obesity, type 1 diabetes or type 2 diabetes.

According to an additional embodiment of the invention, these detoxified flours and semolina, or detoxified gluten or food products obtained through their use, can be advantageously used as protective agents with respect to probiotic microorganisms such as those belonging to the *Lactobacilli* genus, e.g. *Lactobacillus acidophilus* (in particular if added to dairy products for patients with lactose intolerance) and/or with antimicrobial agents with respect to Gram-negative and/or Gram-positive bacteria. Preferably, said Gram-negative bacteria belong to the *Salmonella* genus, still more preferably to the species *Salmonella typhimurium* and said Gram-positive bacteria belong to the *Staphylococcus* genus, still more preferably to the *Staphylococcus aureus* species.

The present invention shall now be described by way of non-limiting illustration, on the basis of the results indicated in the following examples and in the accompanying figures, in which.

Figure 1:
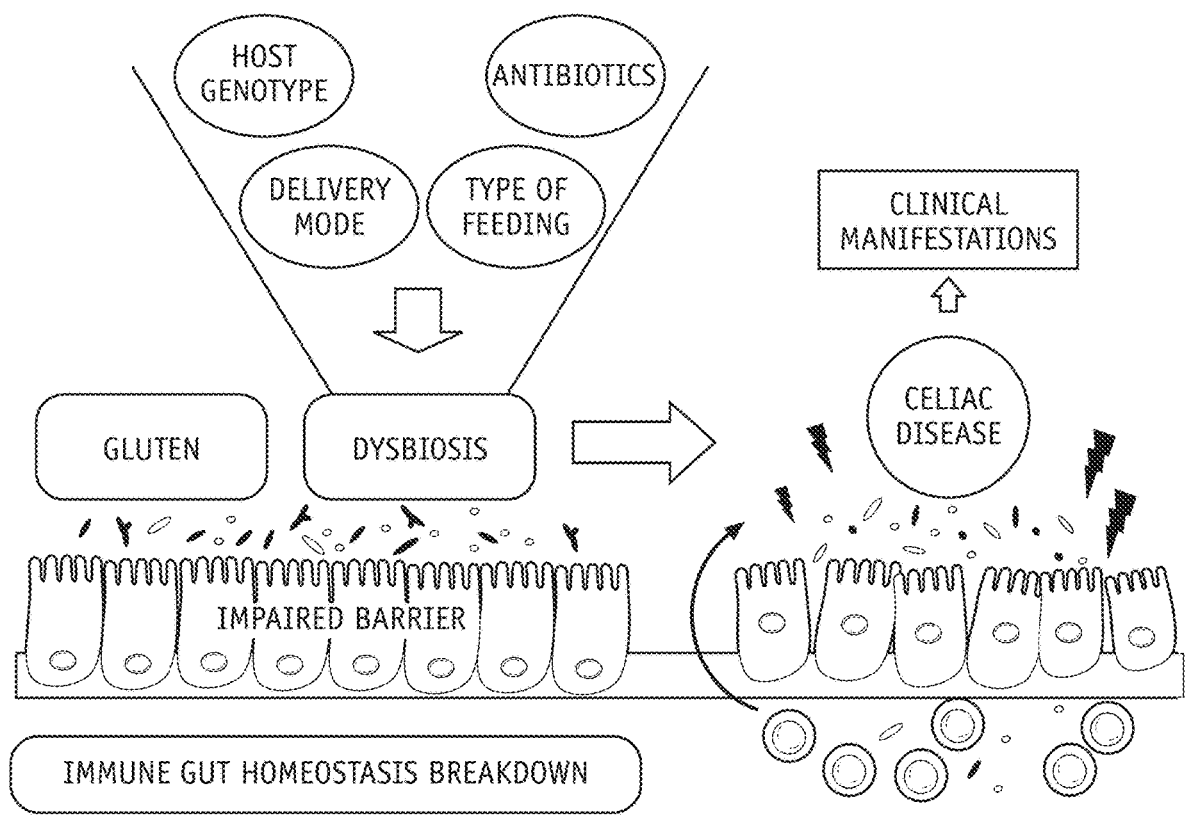
FIG. 1 shows an illustrative diagram of the pathogenesis of the celiac disease (MC).
Figure 2:
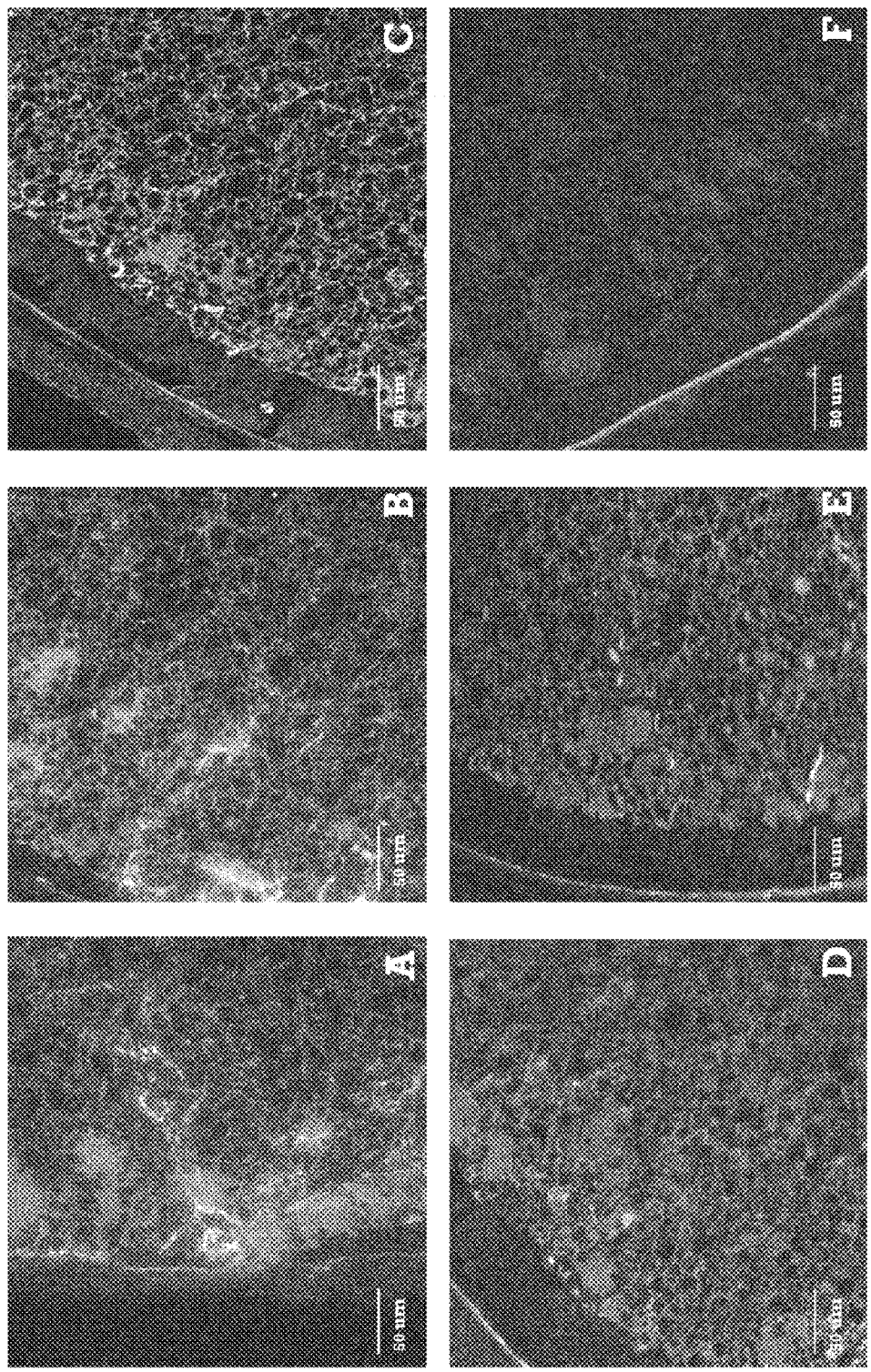
FIG. 2 shows the wheat sections (1 µM) related to the steps of the method of treatment after marking with antibody 06010 which recognizes the protein fractions of gliadins and of low molecular weight glutenins (LMW-GS). Panel A: Step b; panel B: Step c; panel C: Step d; panel D: Step e; panel E: Step f; panel F: Step g of the method according to the invention.
Figure 3:
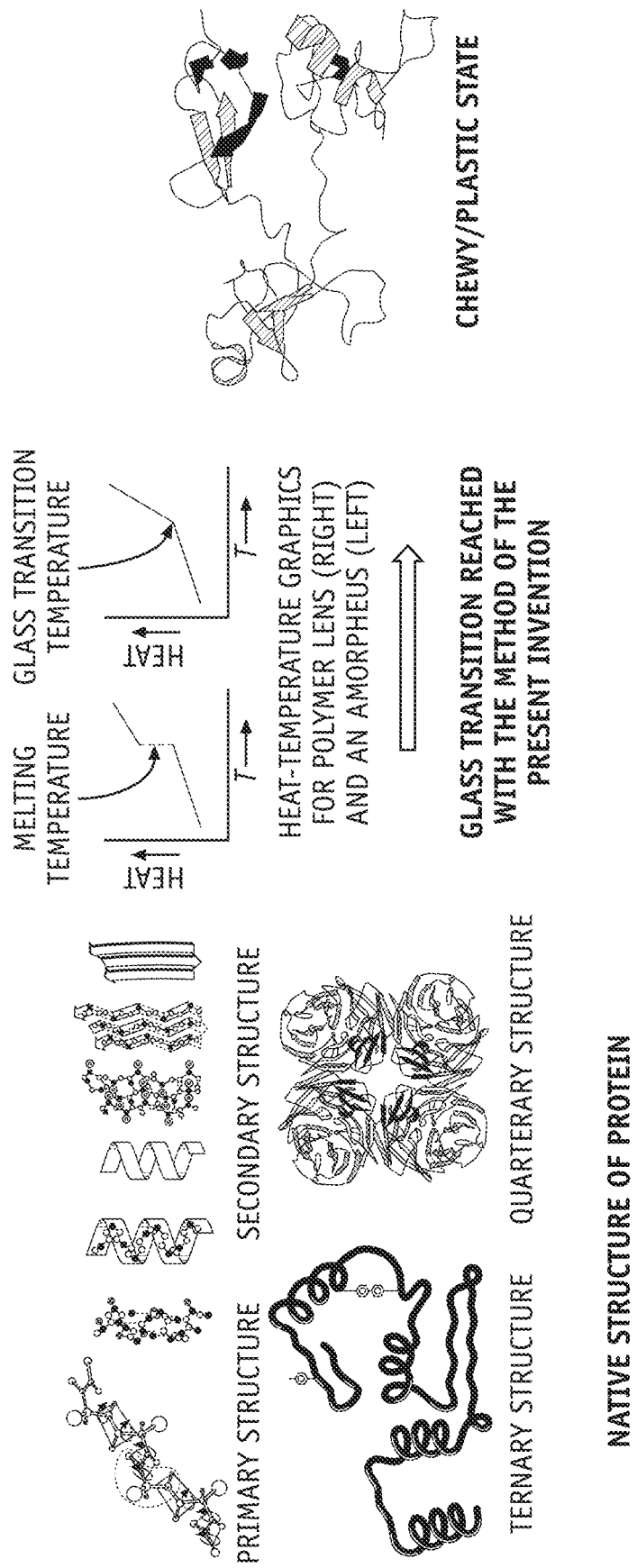
FIG. 3 represents the structure of the protein before and after the heat treatment according to the method of the present invention.
Figure 4:
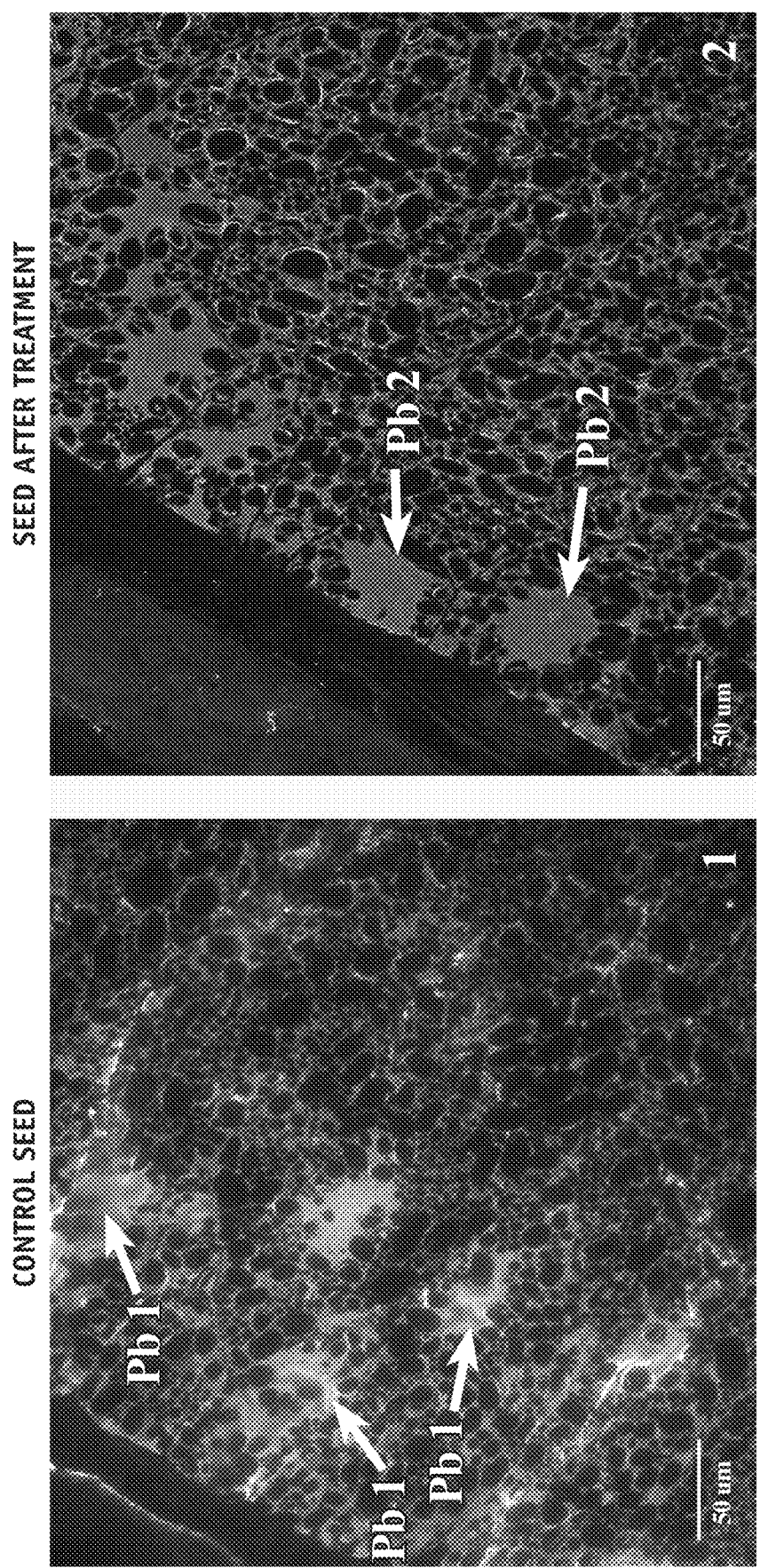

FIG. 4 shows the wheat sections (1 µm) control and after treatment of the method of the present invention. (1) Control wheat section, with a non-homogeneous protein matrix (Pb 1); (2) Wheat section after treatment, with a homogeneous and confluent protein matrix (Pb 2). The non-parametric Friedman test applied to 6 different seeds (4 sections for each seed) detected highly significant differences between the two types of protein bodies (Pb1 and Pb2) in the seeds of the control and after treatment samples.

Figure 5:
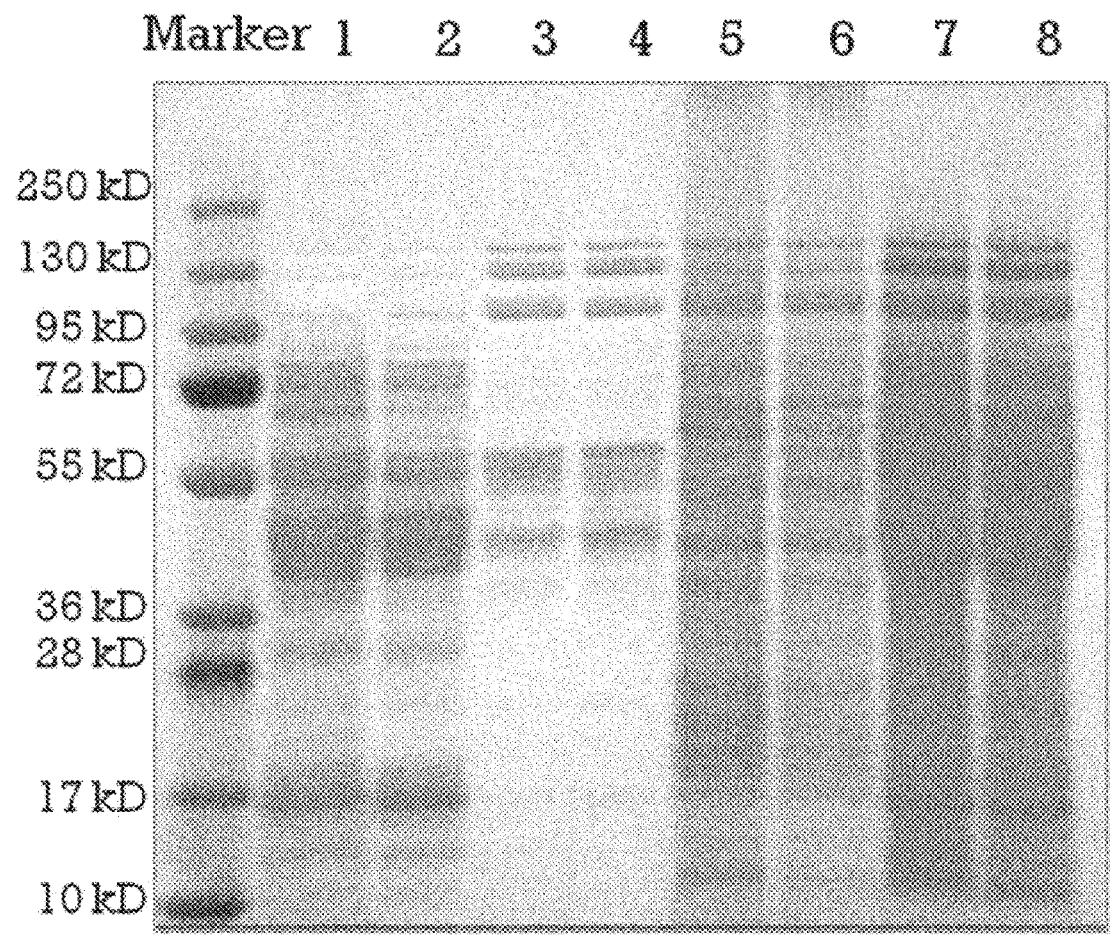

FIG. 5 shows the extraction of the protein fractions and the separation through SDS-PAGE in reducing conditions. Lane 1, gliadins extracted from flour coming from control seeds, which have not undergone the heat treatment of the present invention; lane 2, gliadins extracted from flours coming from seeds treated with the method of the present invention; lane 3, HMW-GS and gliadins extracted from flour coming from control seeds that have not undergone the heat treatment of the present invention; lane 4, HMW-GS and gliadins extracted from flours coming from seeds treated with the method of the present invention; lane 5, glutenins extracted from flour coming from seed control that have not undergone the heat treatment of the present invention; lane 6, glutenins extracted from flours coming from seeds treated with the method of the present invention; lane 7, total proteins extracted from flour coming from control seeds that have not undergone the heat treatment of the present invention; lane 8, total glutenin proteins extracted from flours coming from seeds treated with the method of the present invention.

Figure 6:
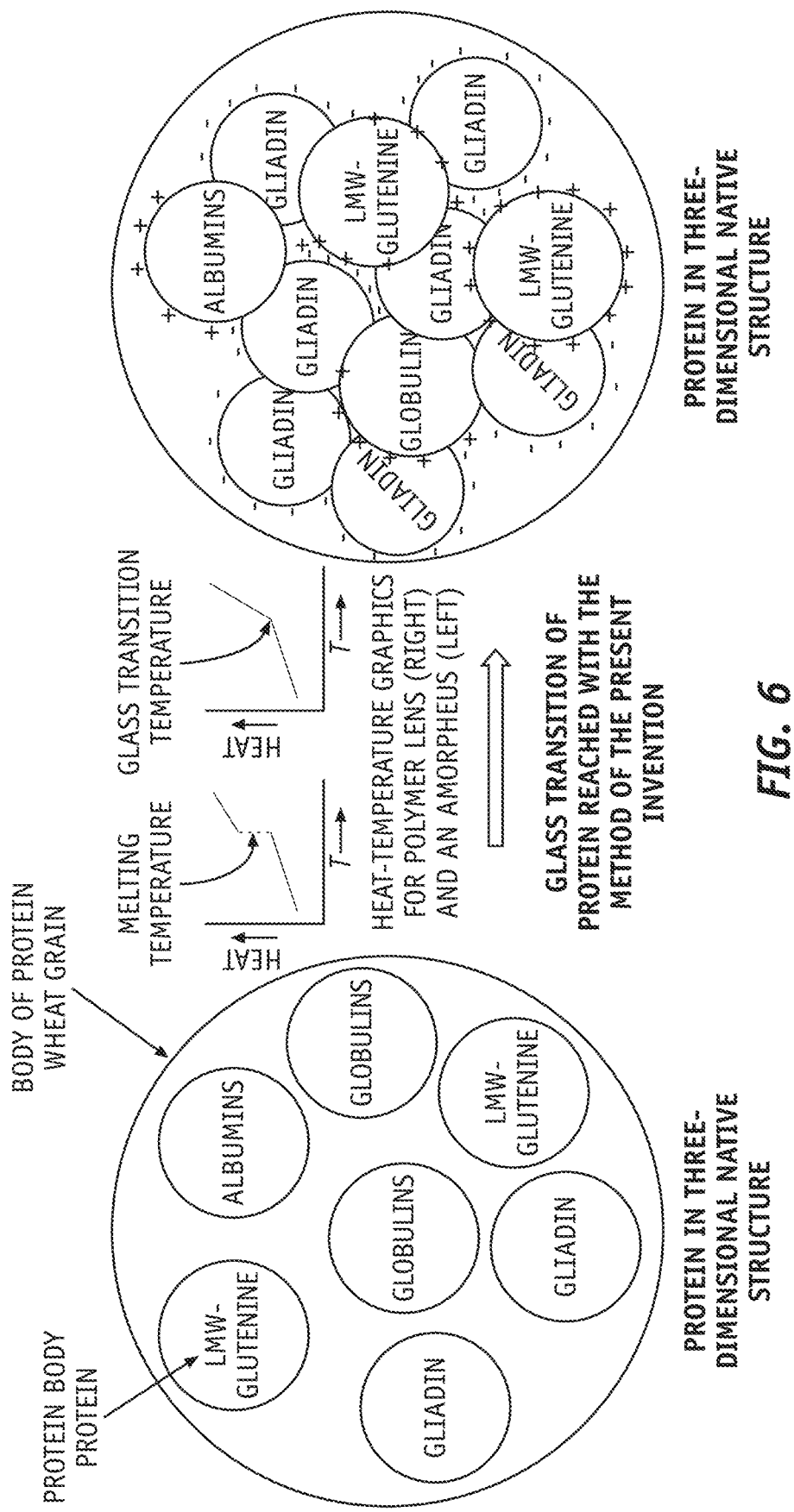

FIG. 6 shows a hypothesis of aggregation between the proteins present in the same protein body and with different charge.

Figure 7:
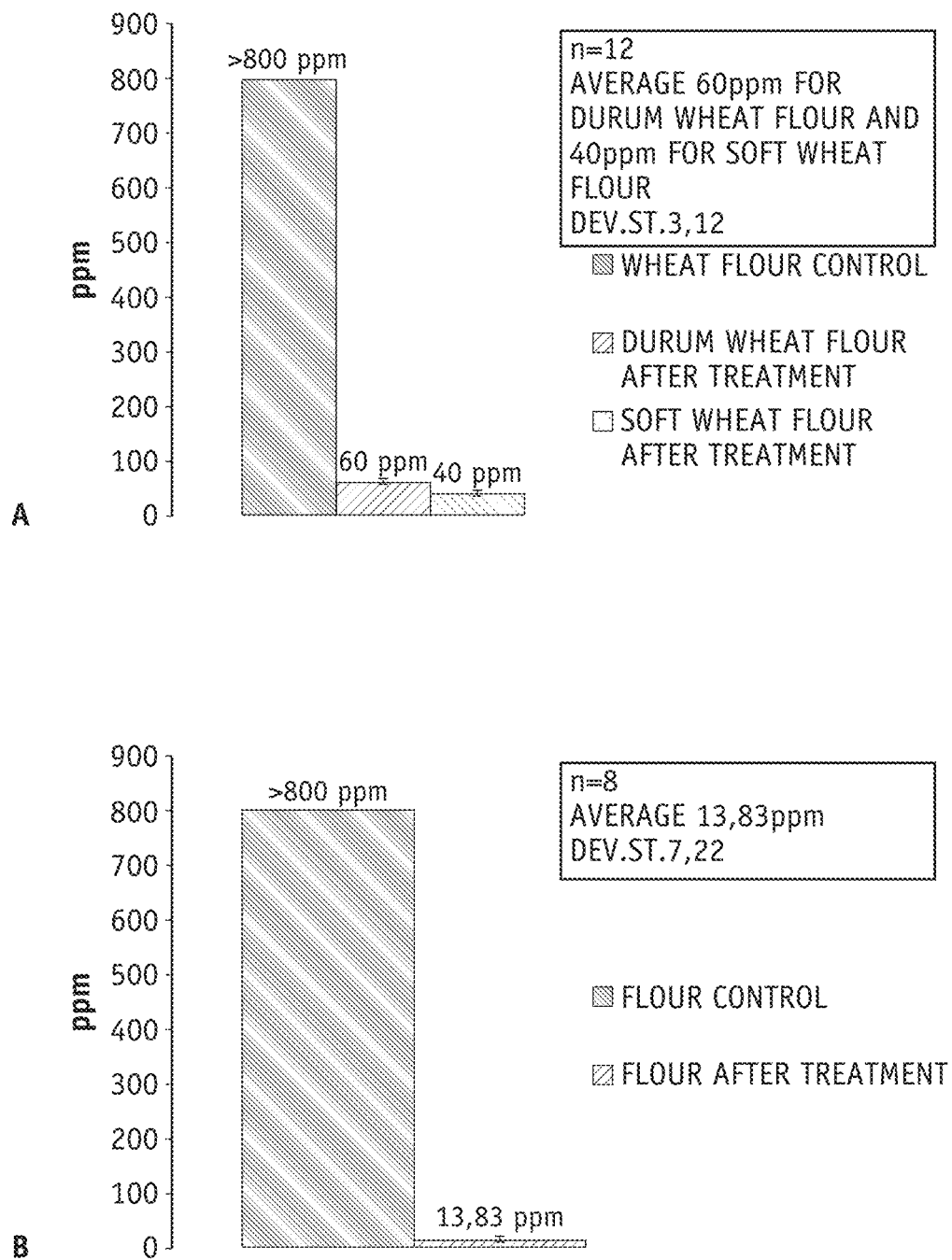

FIG. 7 shows the summary histograms of the ELISA assay with monoclonal antibody R5 Ridascreen Gliadin carried out on samples of control flour and after treatment according to the method of the international patent application WO2014/053891 compared with the method of the present invention.

Figure 8:
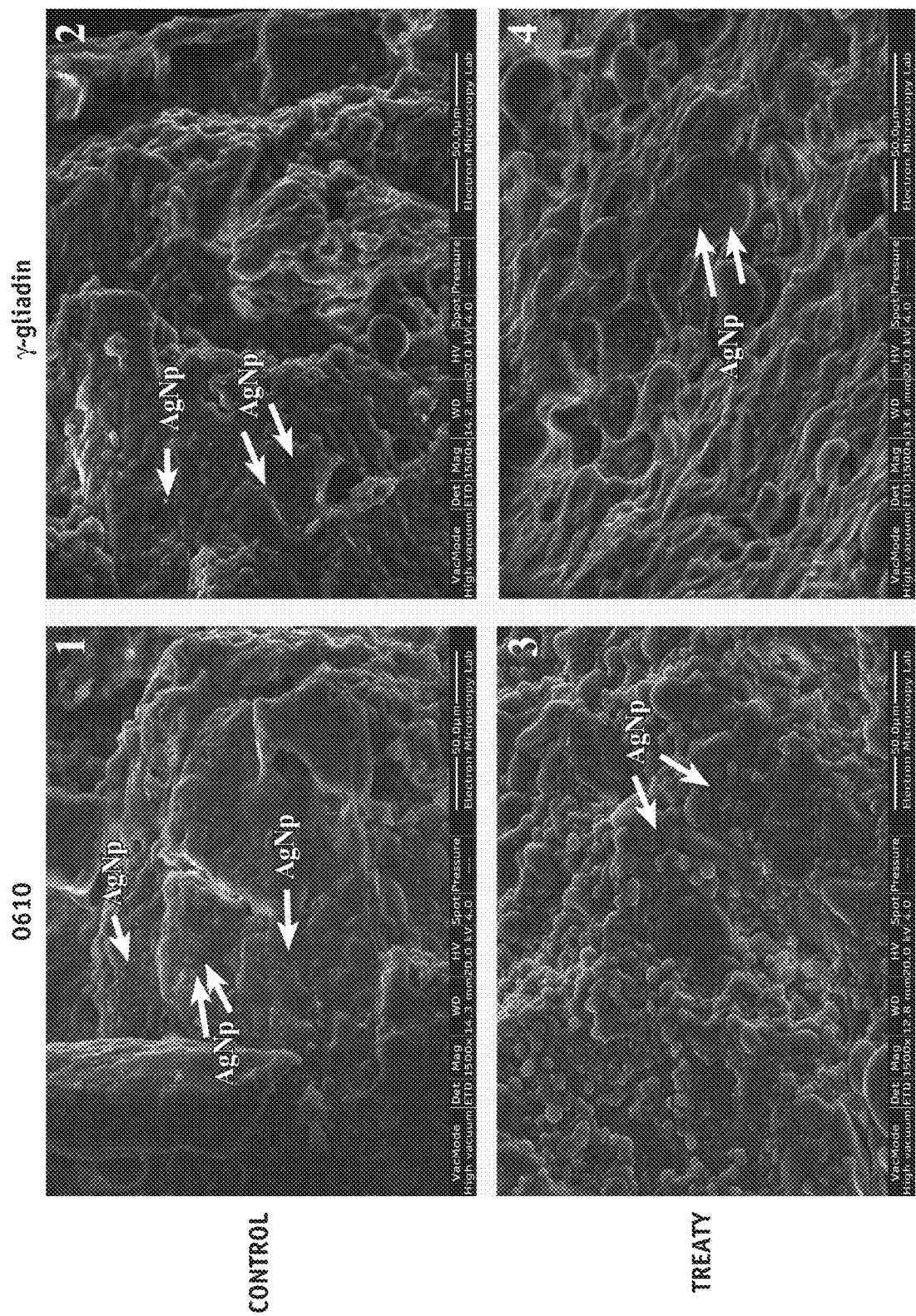

FIG. 8 shows the sections of control wheat (Control) and after treatment (Treated) of the method described in the present invention, cut transversely, and examined through SEM-Immunogold, immunomarked with 0610 antibody and γ-gliadin. 1. Control marked with 0610 antibody; 2. Control after marking with antibody anti γ-gliadin; 3. Treated marked with 0610 antibody; 4. Treated marked with antibody anti γ-gliadin. The arrow in the figure represent the silver particles (AgNp) detected through EDS analysis (Energy Dispersive Spectroscopy).

Figure 9:
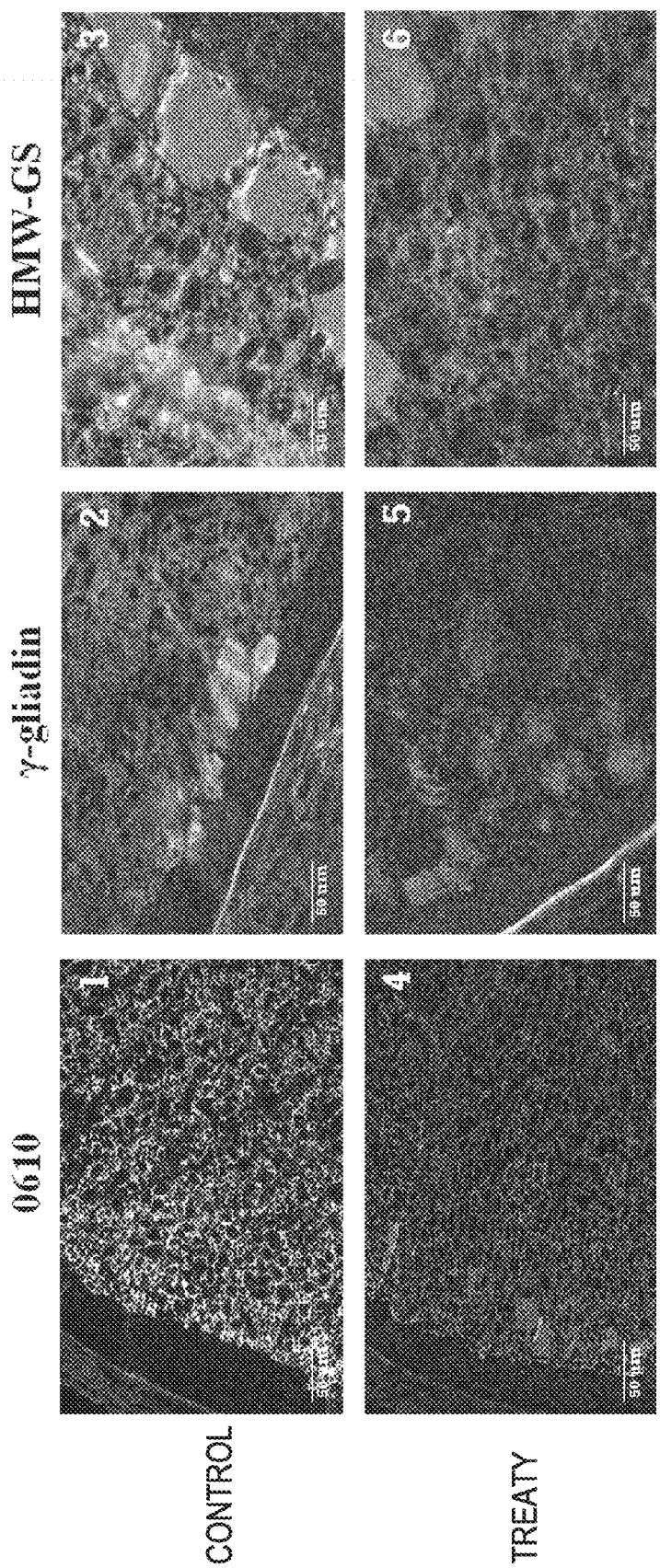

FIG. 9 shows the sections of wheat (1 μm) control (Control) and after treatment (Treated) according to the method of the present invention, marked with the 0610 antibody, HMW-G e γ-gliadin. 1. Control marked with 0610 antibody; 2. Control after marking with γ-gliadin antibody; 3. Control marked with antibody HMW-GS; 4. Treated marked with 0610 antibody; 5. Treated after marking with the antibody γ-gliadin; 6. Treated after marking with the antibody HMW-GS.

Figure 10:
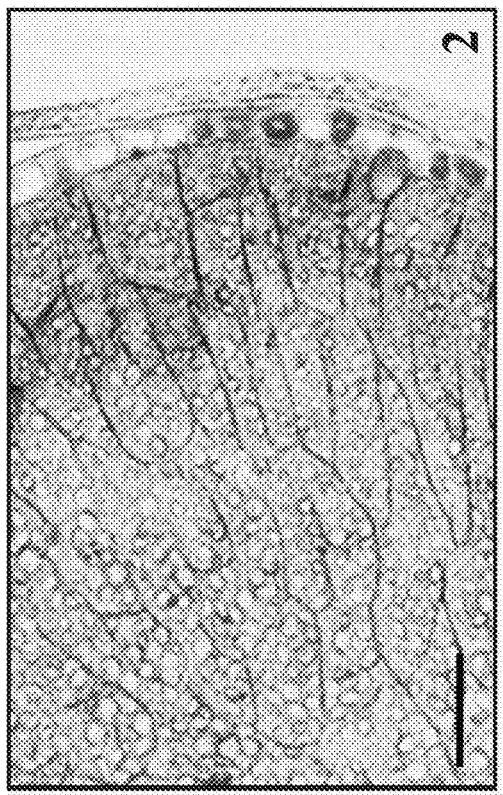
Figure 10:
Figure 10:
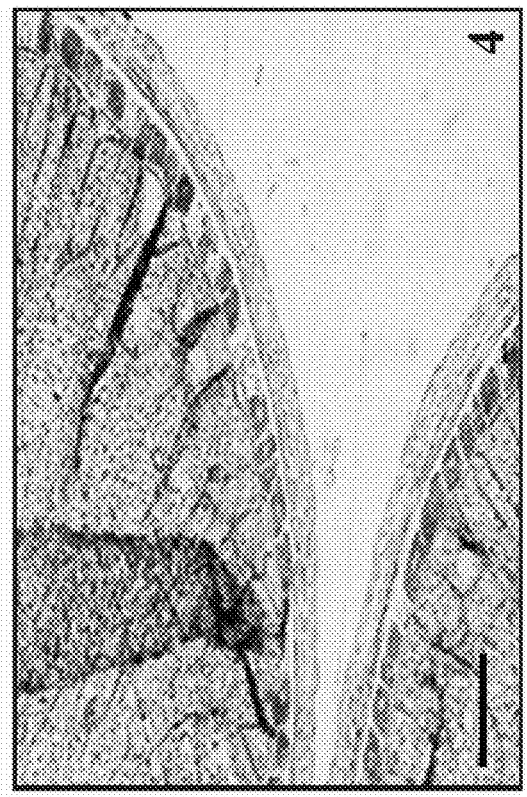
Figure 10:
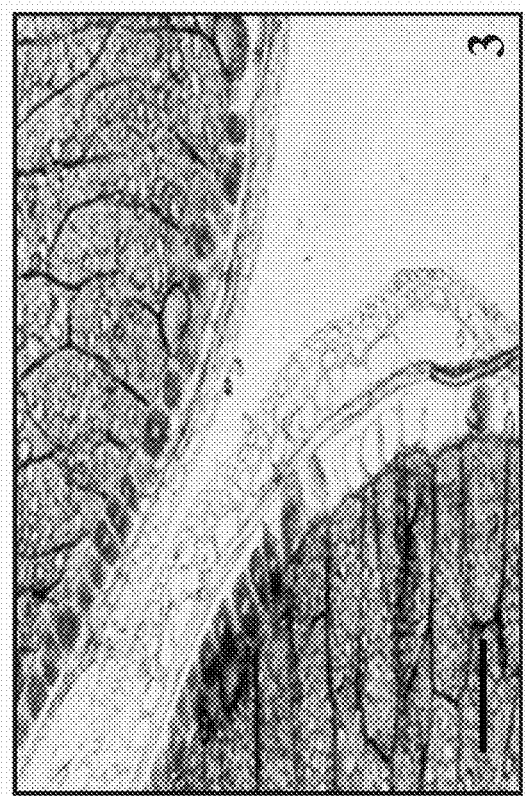

FIG. 10 shows the colorimetric analysis carried out with the monoclonal antibody R5-HRP conjugated, in sections of control and after treatment seeds. 1. Sub-aleurone of the control seed; 2. Sub-aleurone of the seed after treatment according to the method of the present invention; 3. Crease of the control seed; 4. Crease of the seed after treatment according to the method of the present invention. The bars in the figure correspond to 100 μm.

Figure 11:
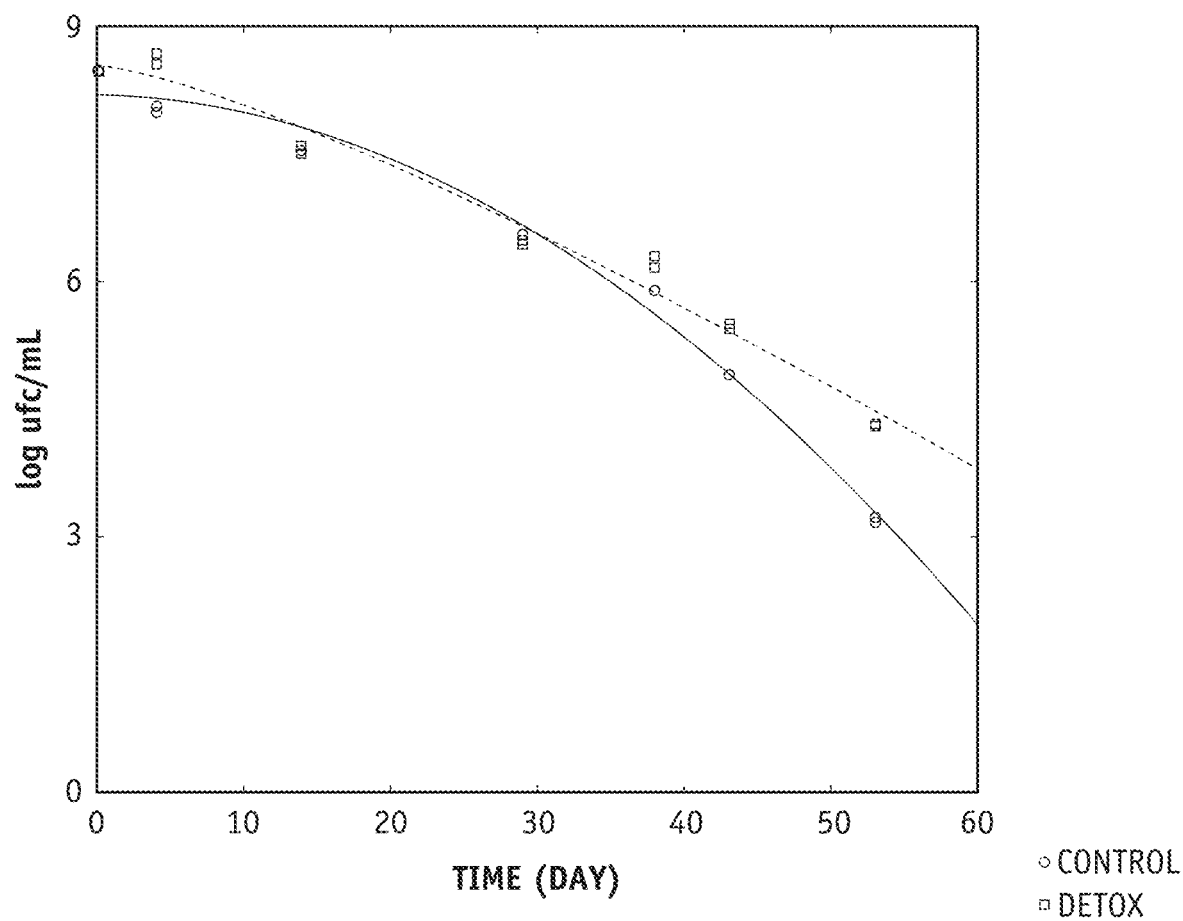

FIG. 11 shows the kinetic analysis of death of *Lactobacillus acidophilus* in saline solution after the addition both of the control bread and of the modified bread (0.8 g/l). The lines represent the best fit through the Weibull distribution.

Figure 12:
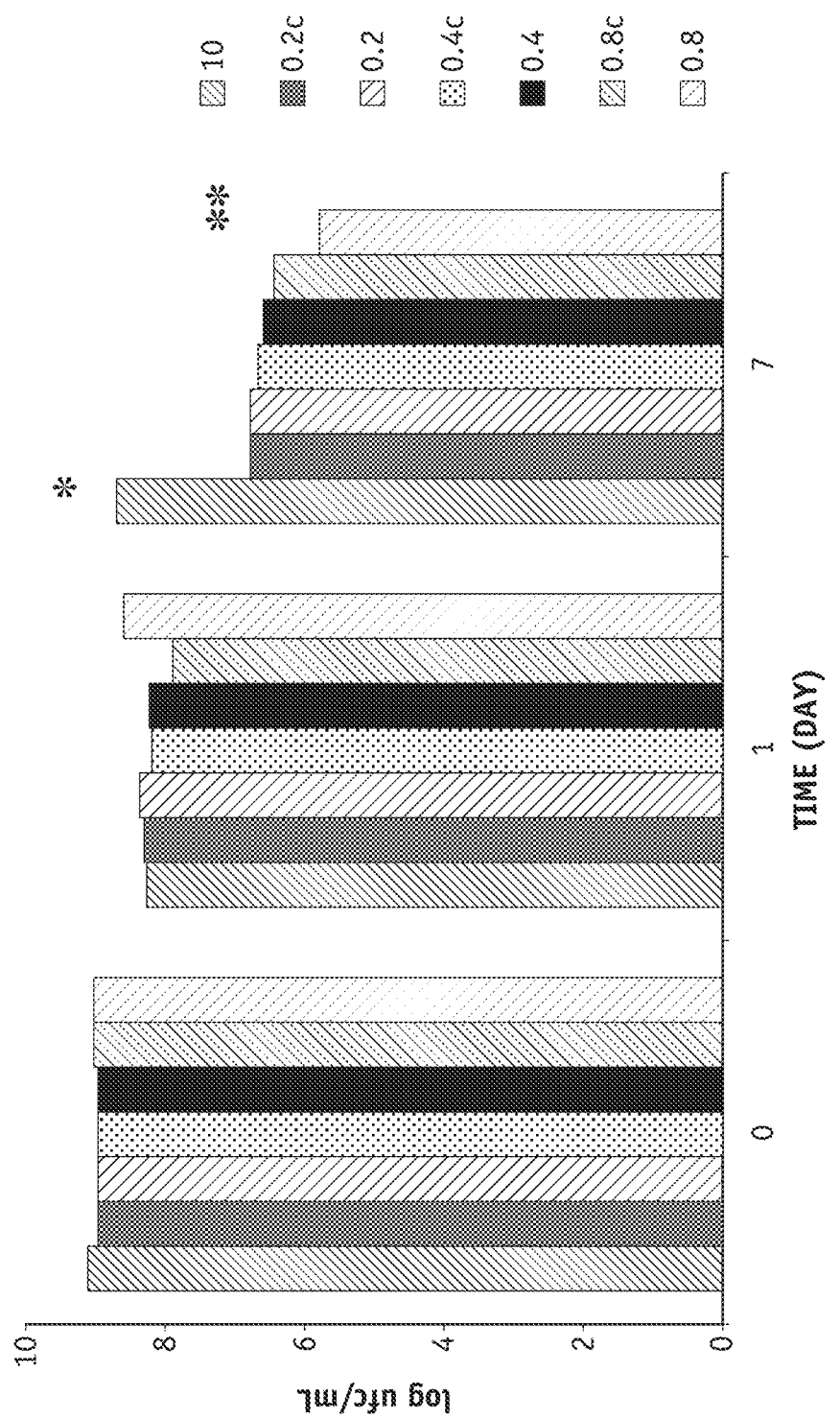

FIG. 12 shows the vital count of *Staphylococcus aureus* in saline solution with the addition of the control bread or of the treated bread (0.2, 0.4 or 0.8 g/l). The mean values±standard deviation. The symbols "*" and "**" identify the significant differences (one-way ANOVA and Tukey's test).

Figure 13:
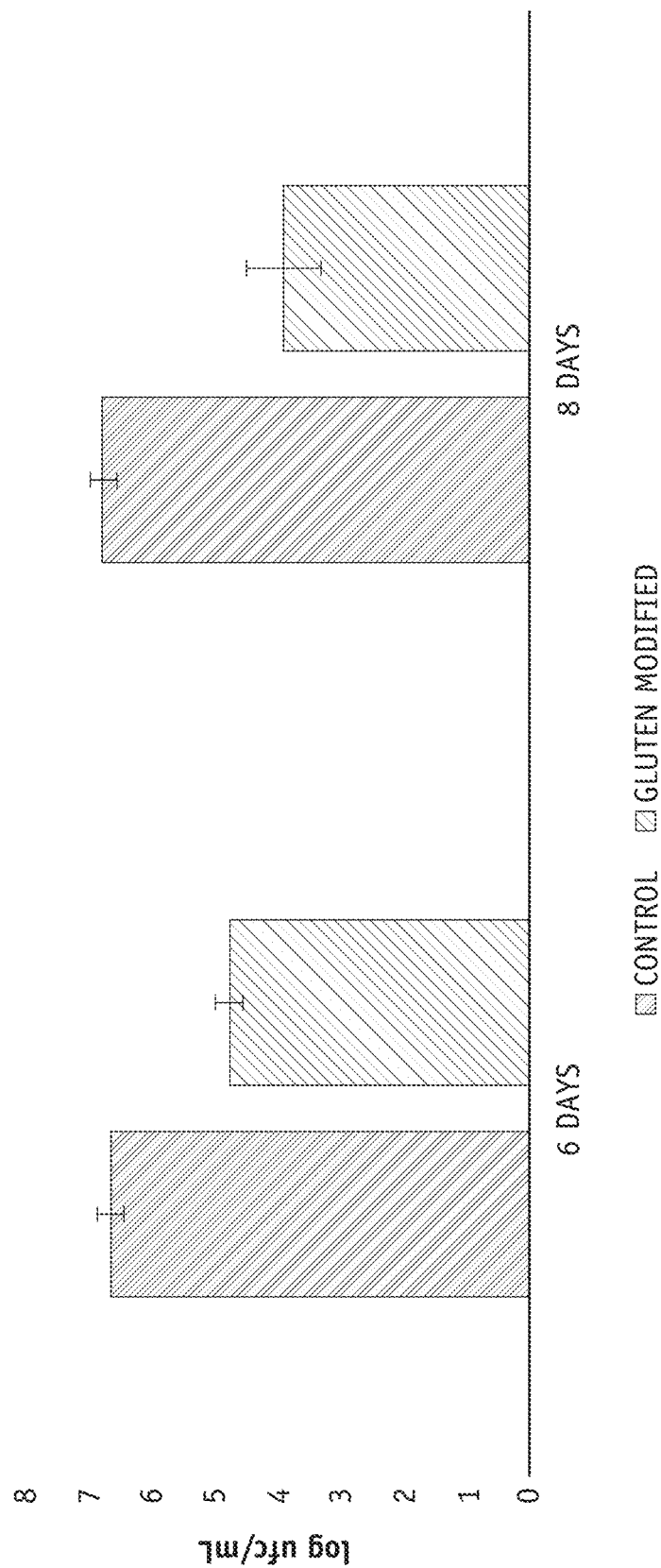

FIG. 13 shows the vital count of *Salmonella* sp. in saline solution with 0.8 g/l of control bread or modified bread added. The mean values±standard deviation.

Figure 14:
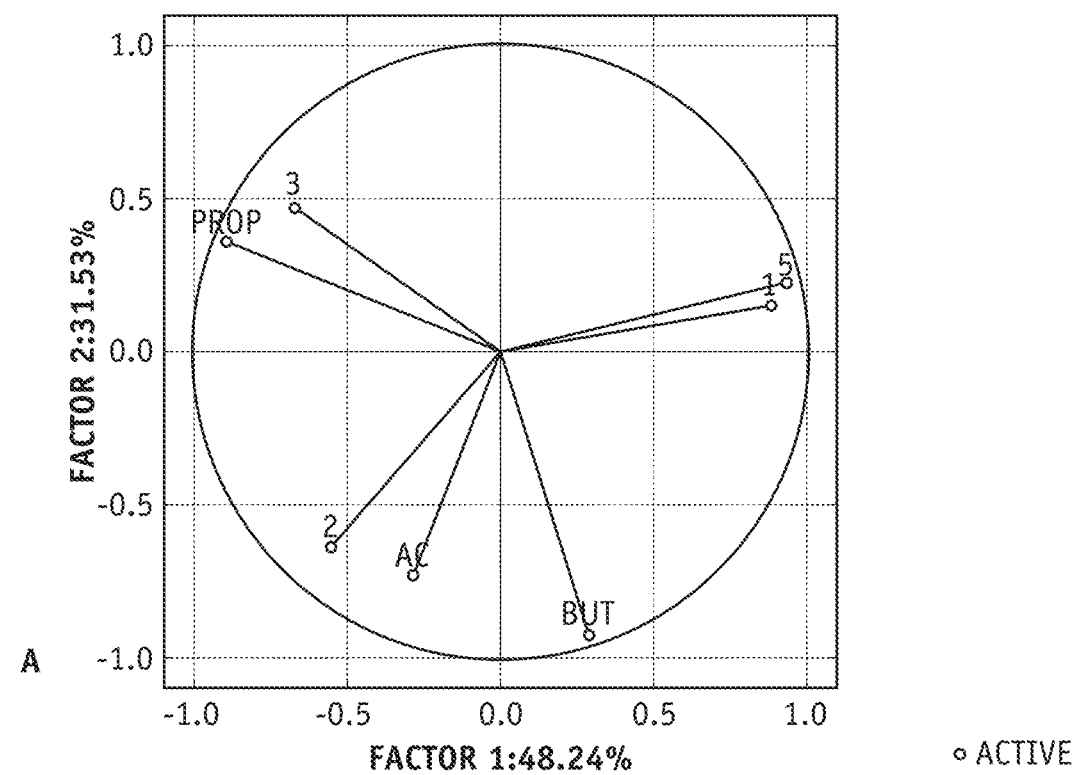
Figure 14:
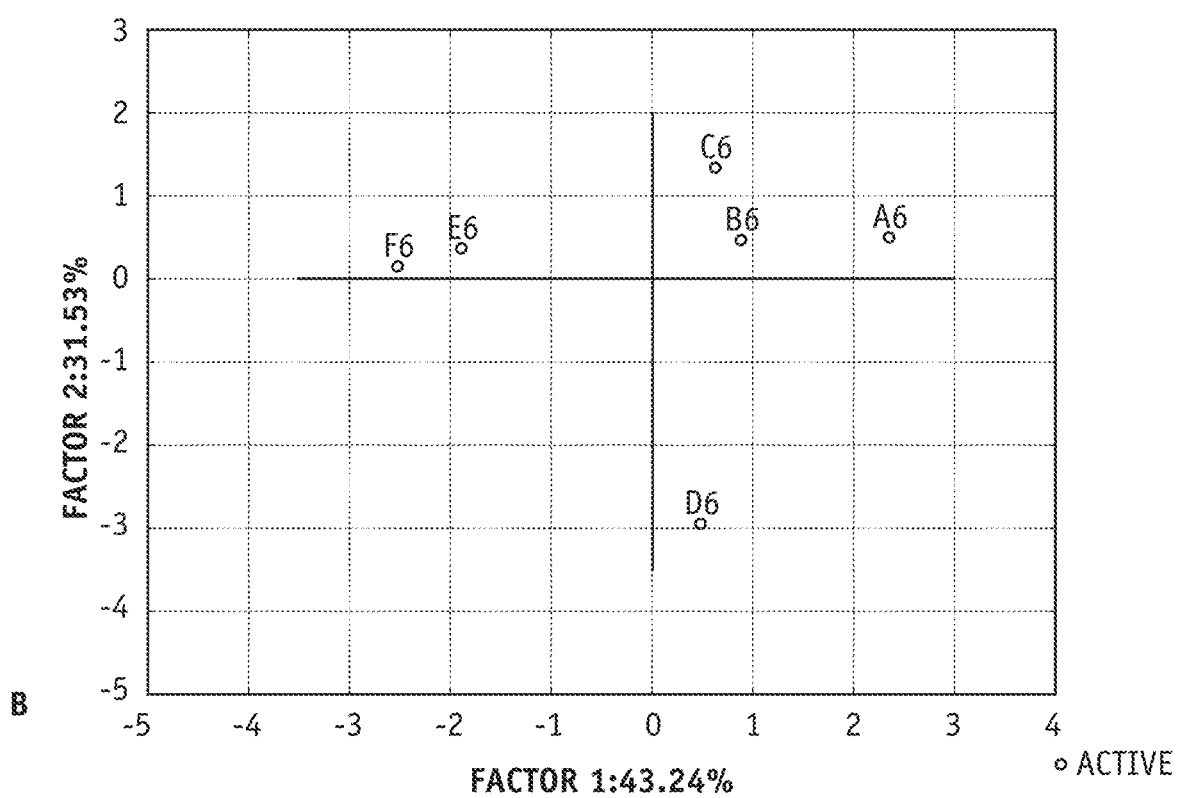

FIG. 14 shows the analysis of the main components relating to the results of the SCFA and FISH after 6 hours of fermentation. Panel A) Projection of the variables; panel B) Projection of the cases. Samples: A, negative control healthy donors; B, healthy donors+control bread; C, healthy donors+modified bread; D, negative control of celiac donors; E, celiac donors+control bread; F, celiac donors+modified bread. Variables: 1, Bif164; 2, Erec482; 3, Bac; 5, lab158; AC: acetic acid; BUT: butyric acid; PROP: propionic.

Figure 15:
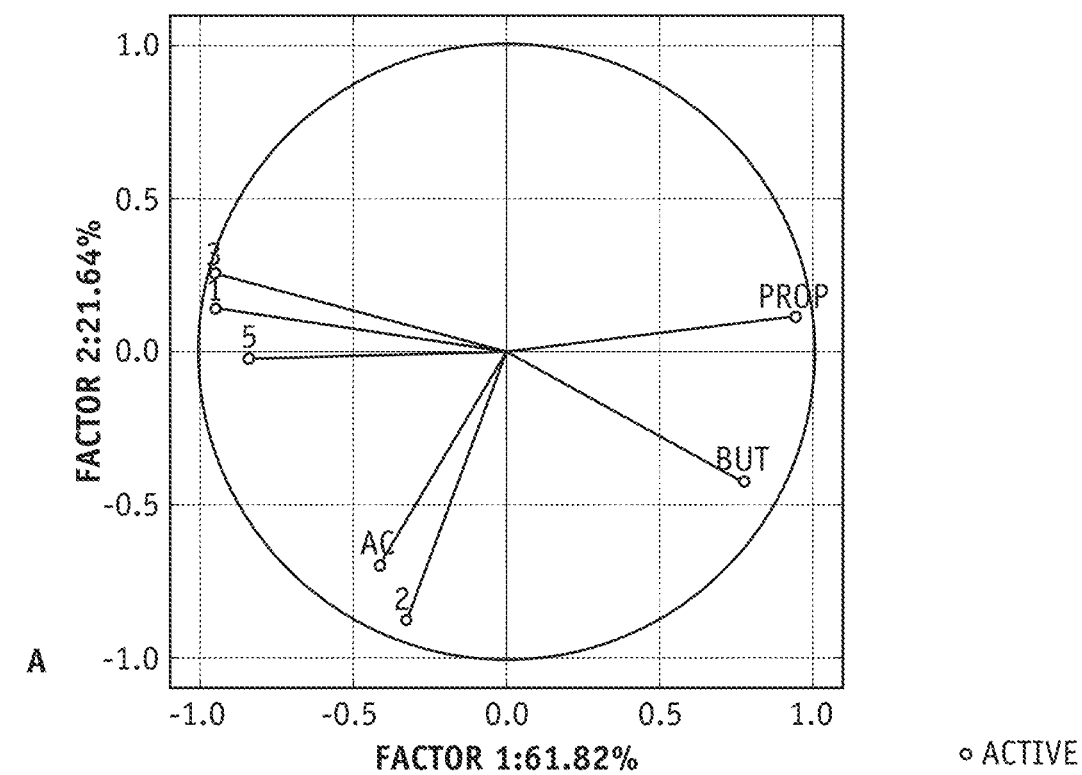
Figure 15:
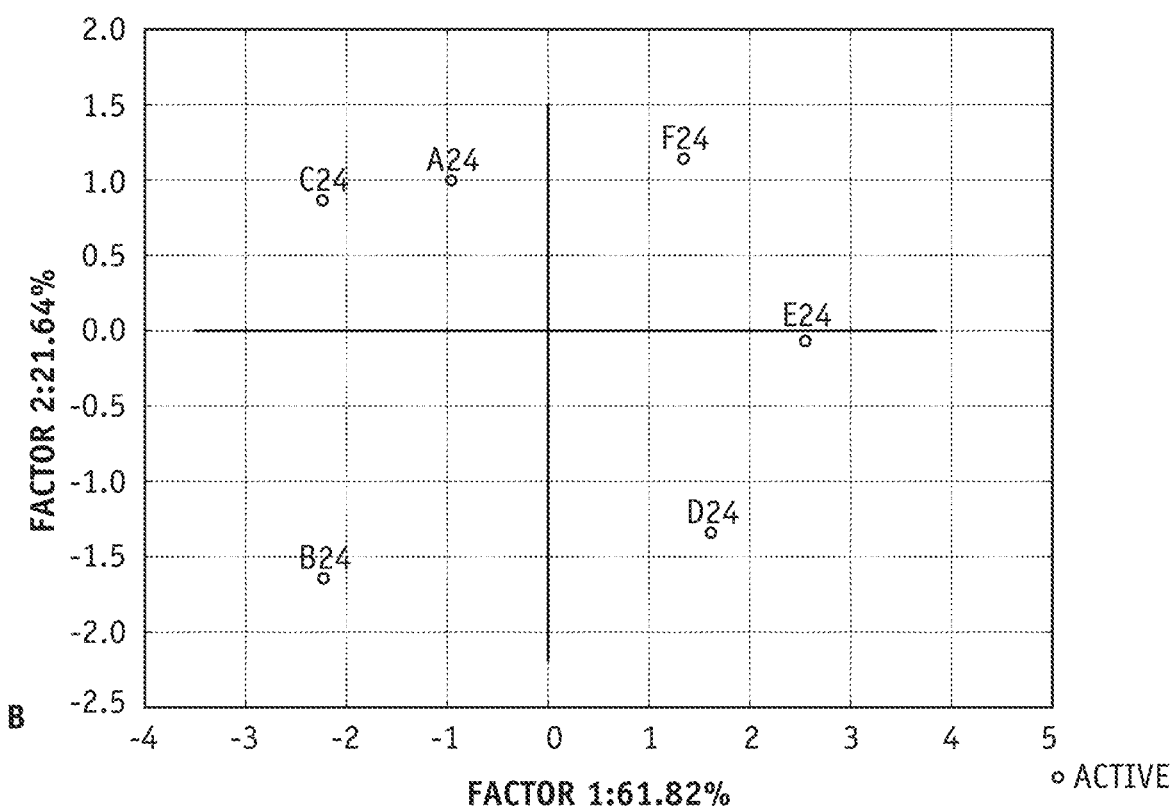

FIG. 15 shows the analysis of the main components relating to the results of the SCFA and FISH after 24 hours of fermentation. Panel A) Projection of the variables; panel B) Projection of the cases. Samples: A, negative control healthy donors; B, healthy donors+control bread; C, healthy donors+modified bread; D, negative control of celiac donors; E, celiac donors+control bread; F, celiac donors+modified bread. Variables: 1, Bif164; 2, Erec482; 3, Bac; 5, lab158; AC: acetic acid; BUT: butyric acid; PROP: propionic.

Figure 16:
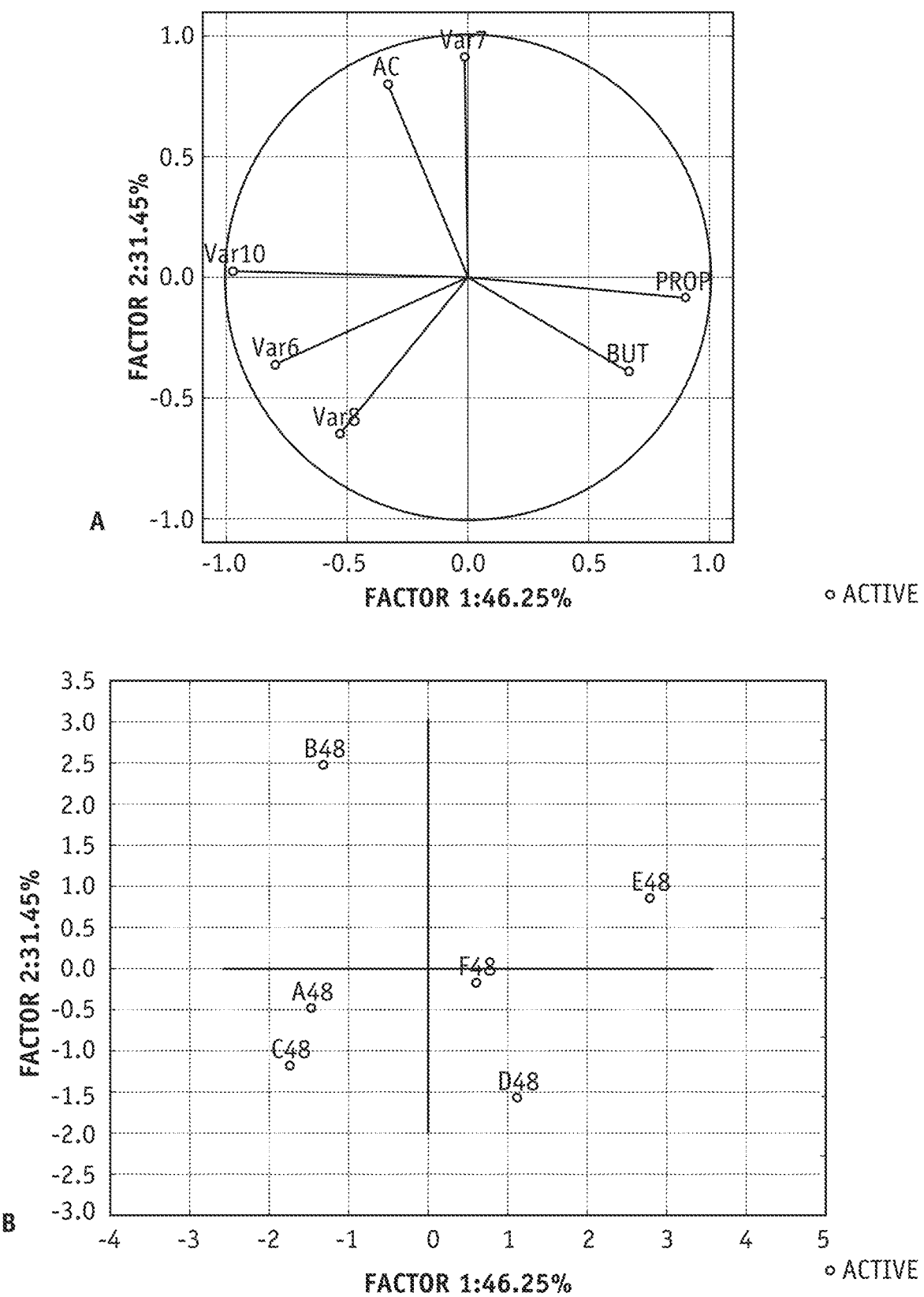

FIG. 16 shows the analysis of the main components relating to the results of the SCFA and FISH after 48 hours of fermentation. Panel A) Projection of the variables; panel B) Projection of the cases. Samples: A, negative control healthy donors; B, healthy donors+control bread; C, healthy donors+modified bread; D, negative control of celiac donors; E, celiac donors+control bread; F, celiac donors+modified bread. Variables: 1, Bif164; 2, Erec482; 3, Bac; 5, lab158; AC: acetic acid; BUT: butyric acid; PROP: propionic.

Figure 17A:
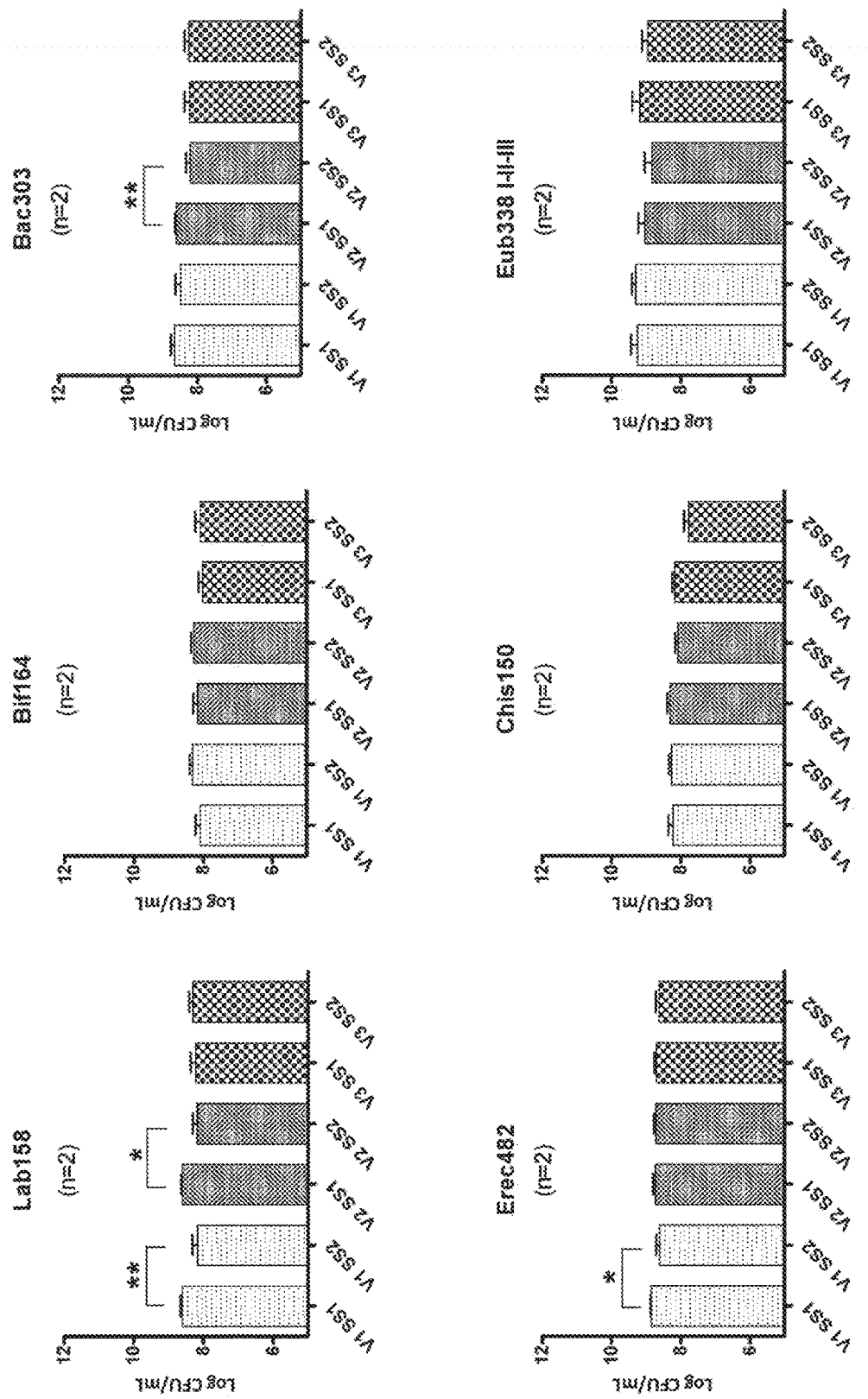
Figure 17B:
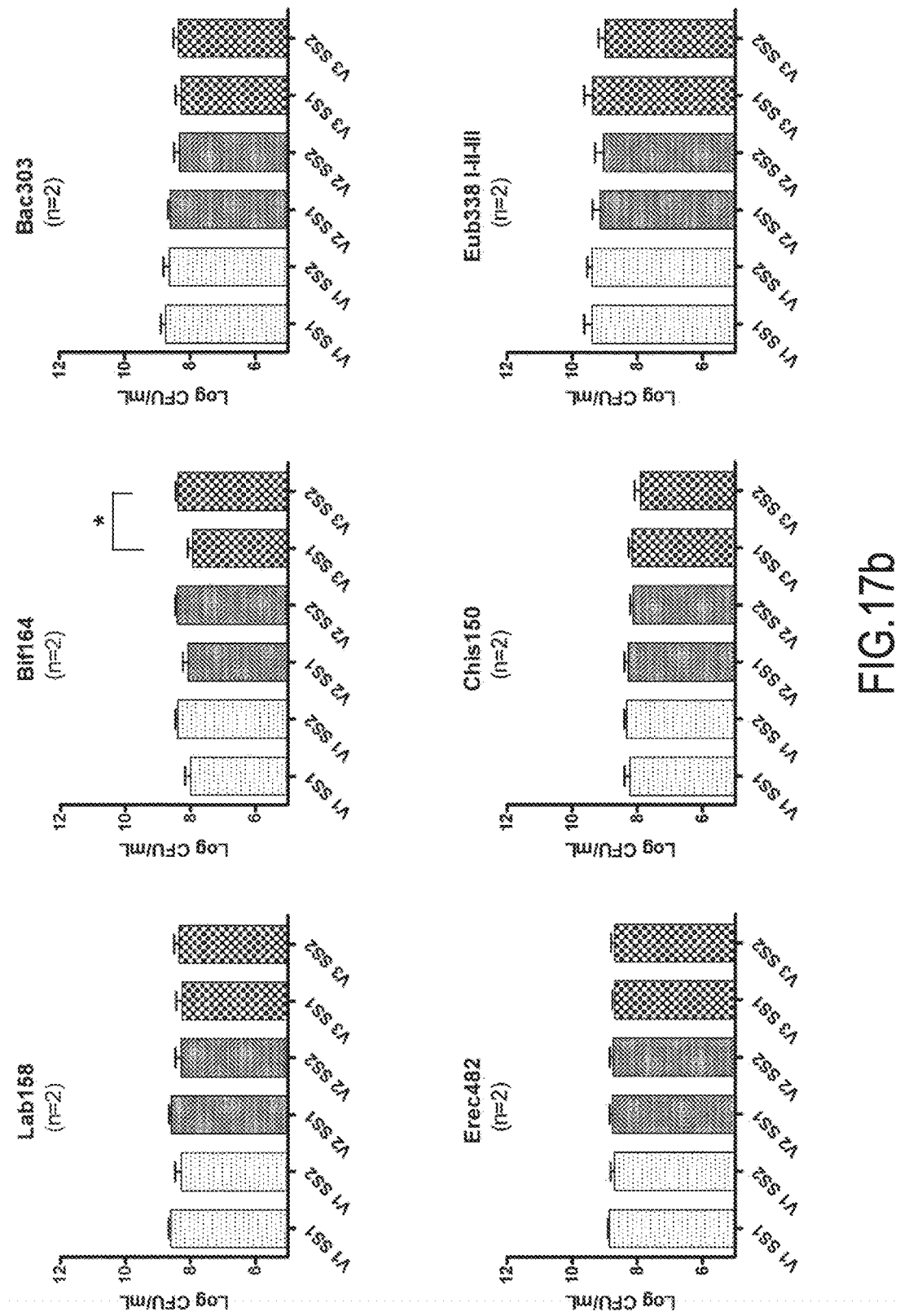

FIG. 17 shows the bacteria groups recovered from the culture broth of three different vessels (V1, V2 and V3) of the model system simulating the parts of the colon before (SS1) and after (SS2) addition of (A) control bread and (B) modified bread in healthy volunteers. Results are reported as data mean of two model systems±SEM (n=2).

Figure 18A:
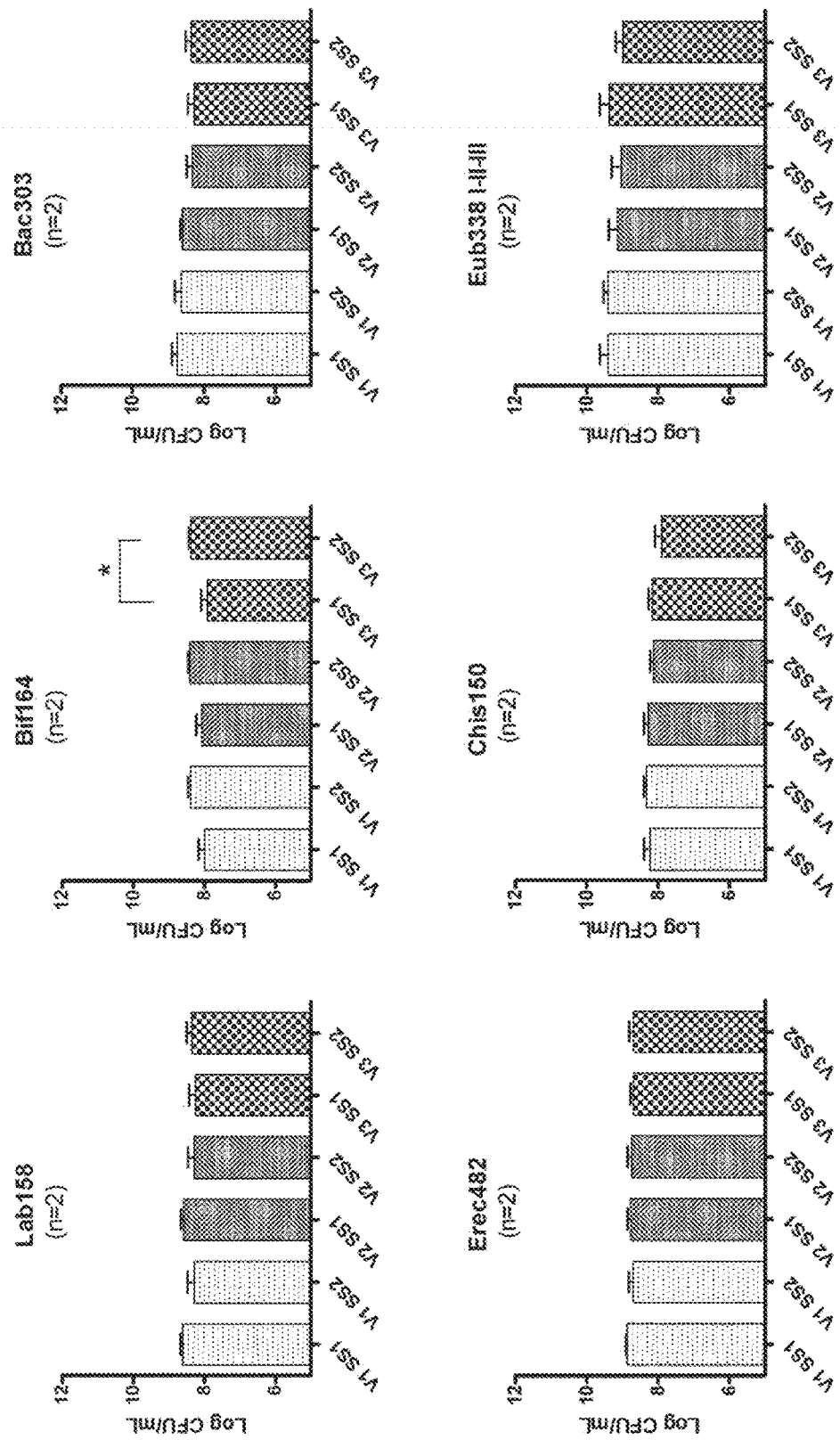
Figure 18B:
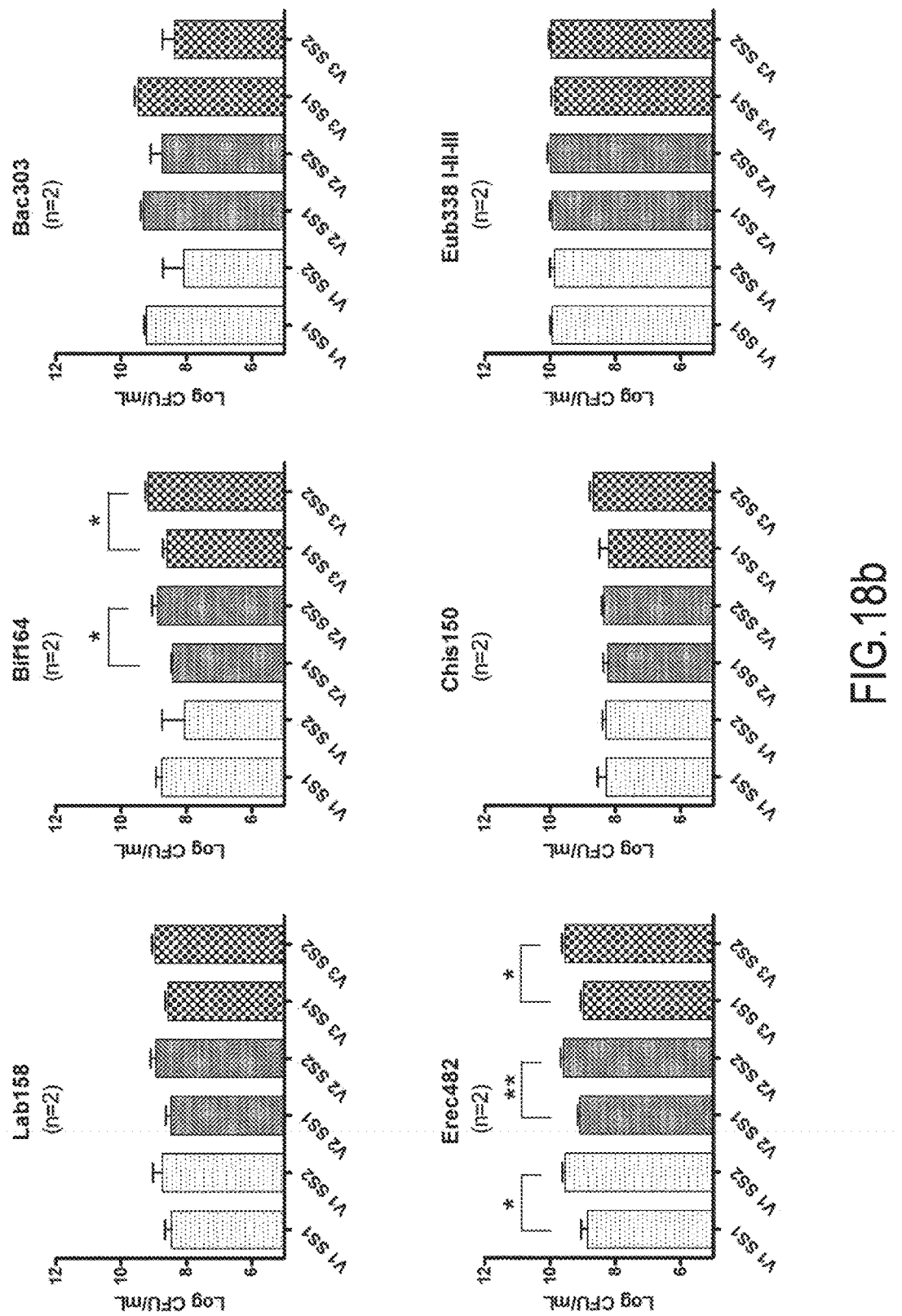

FIG. 18 shows the bacteria groups recovered from the culture broth of three different vessels (V1, V2 and V3) of the model system simulating the parts of the colon before (SS1) and after (SS2) addition of modified bread in (A) healthy patients and (B) celiacs. Results are reported as data mean of two model systems±SEM (n=2).

Figure 19:
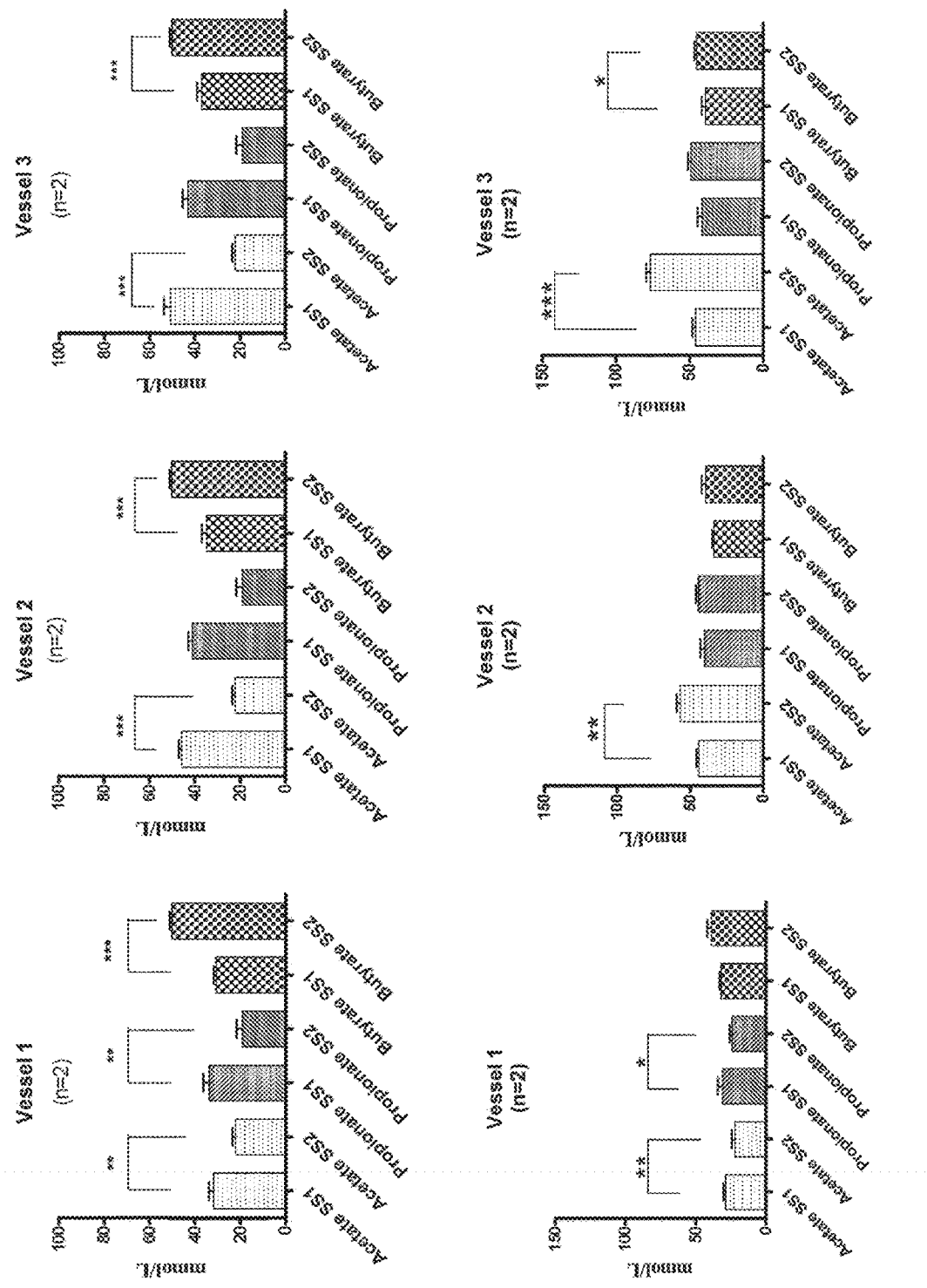

FIG. 19 shows short-chain fatty acids SCFA recovered from the culture broth of three different vessels (V1, V2 and V3) of the model system simulating the parts of the colon before (SS1) and after (SS2) addition of (A) control bread and (B) modified bread in healthy volunteers. Results are reported as data mean of two model systems±SEM (n=2).

Figure 20:
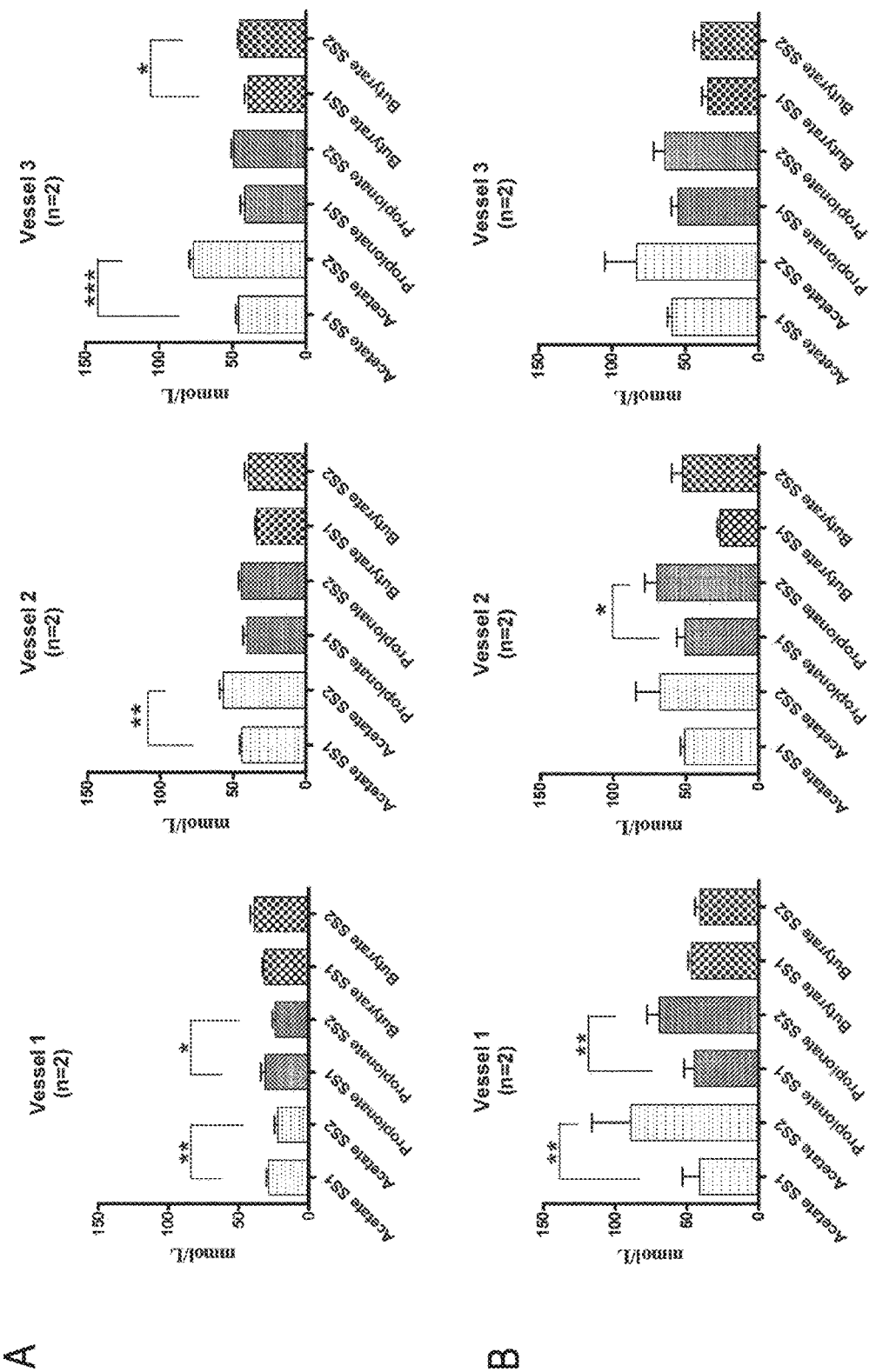

FIG. 20 shows short-chain fatty acids SCFA recovered from the culture broth of three different vessels (V1, V2 and V3) of the model system simulating the parts of the colon before (SS1) and after (SS2) addition of modified bread in (A) healthy patients and (B) celiacs. Results are reported as data mean of two model systems±SEM (n=2).

Figure 21:
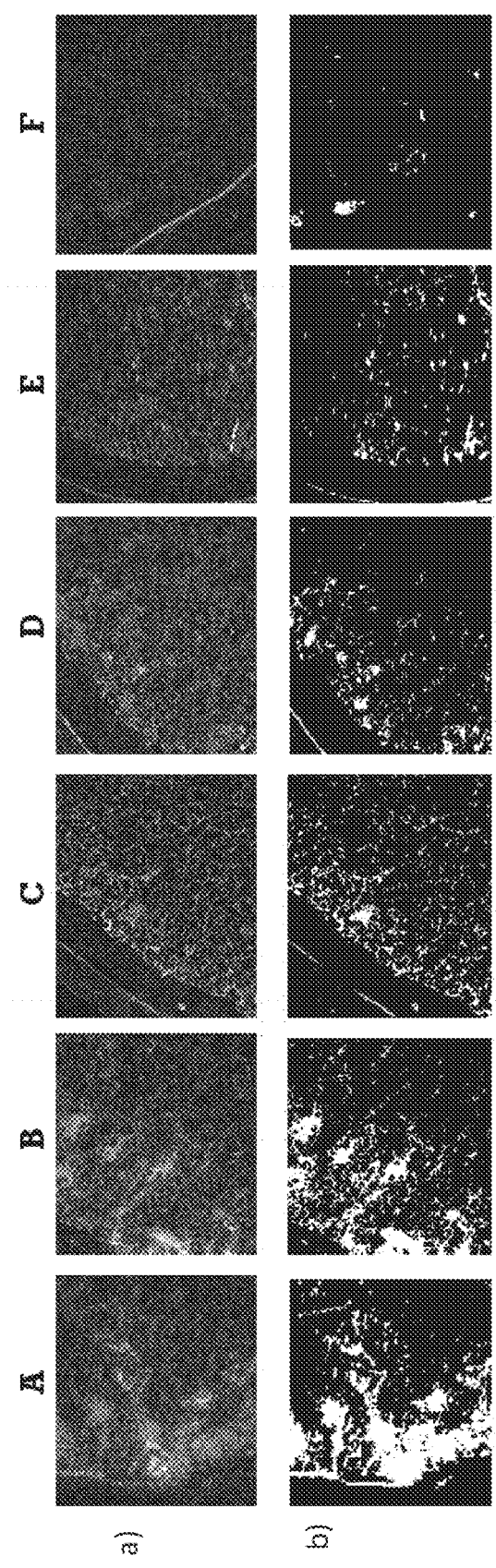
Figure 21:
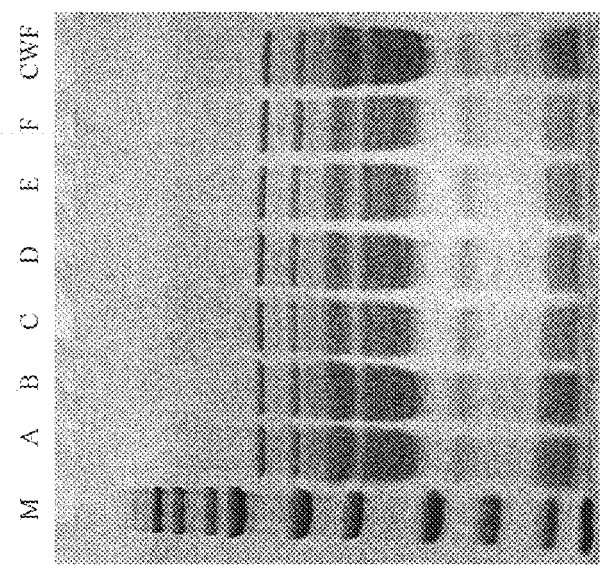

FIG. 21, panel a) shows soft wheat sections (1 μm) relative to the treatment steps after conjugation with 0610 antibody, which recognizes the protein fractions of gliadins and LMW-GS. (A) Step b; (B) Step c; (C) Step d; (D) Step e; (E) Step f; (F) Step g; panel b) shows the image thresholding analysis of the above steps through the use of Image J software; panel c) shows SDS-PAGE analysis of the protein fractions of gliadinsand related weight control flour (CWF) extracted in 70% EtOH. (A) gliadin from step b; (B) gliadin from step c; (C) gliadin from step d; (D) gliadin from step e; (E) gliadin from step f; (F) gliadin from step g; panel d) illustrates a summary Table of the % decrease relative to the values of MGV (Mean Grey Value) obtained from the analysis of microscopy image steps and optical density (OD) relative to SDS-PAGE expressed gliadin protein fractions.

EXAMPLES

Example 1

Reduction of the Antigenicity of the Gluten Proteins After Treatment With the Method According to the Invention After subjecting the wheat grains to the detoxification method according to the invention, the reduction of the antigenicity of the toxic epitopes of the gluten protein on the flours was tested using the official method (ELISA assay with antibody R5) adopted by the barred ear laboratories for the recognition of gluten in flours and products intended for celiac patients.

In particular, the gluten proteins previous denatured with the Mendez cocktail were extracted from the flours by means of alcohol solution and tested according to the R5 sandwich ELISA method (see FIG. 7) using the monoclonal antibody R5 that recognizes the toxic peptide sequence QQPFP, which is found repeated in the gluten proteins. FIG. 7, (panel A) shows the summary histograms of the ELISA assay with R5 Ridascreen Gliadin, of the samples treated with the method described in the international patent application WO2014/053891 compared to the method of the present invention (panel B). Incidentally, the flour samples coming from the grains treated with the method described in the international patent application WO2014/053891 exhibited a reduction in the antigenicity of the toxic epitope QQPFP in the range between 60 and 40 ppm (panel A, FIG. 7; Lamacchia C. et al. 2016). Instead, the flours coming from the grains treated with the method of the present invention show a significant reduction in the antigenicity of the toxic epitope to 13.83±7.22 ppm, enabling these flours to be considered, for all purposes of the law, "gluten free" flours, although the gluten is still present within them.

The improvement of the detoxification of the gluten protein from the cereal grains according to the present invention consists of the reduction in the antigenicity of the toxic epitopes of gluten to a range between 0 and 20 ppm, making them far safer for celiac patients. This reduction was not achievable through the method of the international patent application WO2014/053891 because in this method the microwave step for 120 seconds, followed by slow cooling at ambient temperature, does not assure the complete modification of the proteins to the plastic form, which instead is reached completely thanks to the steps of the method described in the present invention.

The changes induced by the method according to the present invention enable the reduction in the antigenicity of the gluten proteins so that they are no longer recognizable even by their own antibodies. To demonstrate this, three samples of control seeds (CWS) and treated seeds (TWS) were cut transversely, and examined through immunogold (FIG. 8), immunofluorescence (FIG. 9) and colorimetric microscopy (FIG. 10) using three specific monoclonal antibodies for the gliadin fraction:

IFRN 0610, monoclonal antibody that recognizes an epitope (QQSF) common to many gliadins;

LMW-GS, murine monoclonal antibodies, which recognizes a repetitive domain present in the fraction of γ gliadin (PEQPFPQGC);

R5, monoclonal antibodies R5 recognizes the highly toxic sequence QQPFP, which is present repeated in gluten proteins.

FIG. 8 shows the sections of control wheat (Control) and after treatment (Treated) of the method according to the present invention, cut transversely, and examined through SEM-Immunogold, immunomarked with 0610 antibody and γ-gliadin. The values obtained in 5 sections coming from 5 different Control and Treated seeds were compared with Student's T-test. The differences observed with the two types of antibody were found to be highly significant (p<0.001).

With the antibody 0610, a decrease of 89% was obtained in the treated seeds compared to the control seeds and a decrease of 87.5% was obtained compared to the antibody γ-gliadin.

FIG. 9 shows the sections of wheat (1 µm) control (Control) and after treatment (Treated) according to the method of the present invention, marked with the 0610 antibody, HMW-G and γ-gliadin. Three different samples (3 sections for each seed) coming from samples of control and after treatment seed were analyzed using the Imagej software. For each image, converted into grey scale, the respective MGVs (mean grey values) were obtained. With the 0610 antibody, a decrease of 91.7% was observed in the treated seeds compared to control seeds and a decrease of 90.6% was observed compared to the antibody γ-gliadin. Thereafter, the two-way Anova test was carried out, with decomposition hypothesis for two variables (type of sample and type of treatment). Among the parameters analyzed, the type of treatment undergone by the seed was the most important factor. The data obtained were found to be highly significant (p<0.001).

FIG. 10 shows the colorimetric analysis carried out with the monoclonal antibody R5-HRP conjugated, in sections of control and after treatment seeds. Three different samples (3 sections for each seed) coming from samples of control and after treatment seed were analyzed using the Imagej software. For each image, converted into grey scale, in binary format, the respective MGVs (mean grey values) were obtained. A decrease of 89.2% was observed in the seed after treatment compared to the control seed, at the level of the sub-aleuronic region, and a decrease of 82% was observed at the fold level. Thereafter, the two-way Anova test was carried out, with decomposition hypothesis for two variables (type of sample and type of treatment). Among the parameters analyzed, the type of treatment undergone by the seed was the most important factor. The data obtained were found to be highly significant (p<0.001).

Example 2

In Vitro Study on the Protective Effect of the Digested Bread Prepared With the Flours Treated According to the Method With Respect to *Lactobacillus acidophilus* and on the Antimicrobial Effect With Respect to *Staphylococcus aureus* and of *Salmonella Typhimurium*

Two different series of experiments were carried out, as shown in the following Table 1.

In particular, the aliquots of physiological solution (NaCl 0.9%) (50 ml) were supplemented with different aliquots of control bread or bread whose flour derives from the milling of the seeds whose gluten was modified with the method described above, digested in vitro in appropriate conditions according to the procedures described by Maccaferri S. et al. (2012) dehydrated and inoculated at 8 log ufc/ml; the samples were then analyzed to periodically assess the vital count by plating on MRS agar (*Lactobacillus acidophilus* and *Bifidobacterium animalis*) or TSA (pathogens) and incubated at 37° C. for 2-4 days. The lactic bacteria were analyzed in anaerobic conditions.

TABLE 1

| | | | |
|---|---|---|---|
| Death kinetics | Lactobaccilus acidophilus Bifidobacterium animalis | Saline solution and samples with the addition of 0.4 or 0.8 g/l of control bread or bread prepared with flour from seeds treated according to the method of the present invention | 7 days (microorganism count every 6-10 hours) |
| Effect of the concentration | Lactobaccilus acidophilus Bifidobacterium animalis | Saline solution and samples with the addition of 0.8 or 5 g/l of control bread or bread prepared with flour from seeds treated according to the method of the present invention | 24 hour |
| Pathogens | Salmonella Typhimurium Staphylococcus aureus | Saline solution and samples with the addition of 0.2, 0.4, or 0.8 g/l of control bread or bread prepared with flour from seeds treated according to the method of the present invention | 7 days (microorganism count after 1 and 7 days) |

Table 2 shows the fitness parameters for the Weibull distribution for the death kinetics of *Lactobacillus acidophilus* (mean±standard values). For each parameter, the letters indicate the significant differences (ANOVA and Tukey's test, P<0.05). The death kinetics showed a downward curve with a shape parameter >1.

TABLE 2

| Samples | log $N_0$* | Δ | p | d.t. | R |
|---|---|---|---|---|---|
| Control 0.4 g/l | 8.43 ± 0.14A | 17.99 ± 0.90A | 1.62 ± 0.15A | 67.46 ± 2.06A | 0.995 |
| Detox 0.4 g/l | 8.38 ± 0.13A | 17.43 ± 2.06A | 1.40 ± 0.14A | 80.53 ± 2.03B | 0.994 |
| Control 0.8 g/l | 8.19 ± 0.12A | 23.40 ± 2.00B | 1.94 ± 0.20A | 70.28 ± 2.63A | 0.993 |
| Detox 0.8 g/l | 8.56 ± 0.14A | 17.57 ± 2.70A | 1.27 ± 0.17A | 93.96 ± 4.00C | 0.990 |

The addition of the saline solution both in the control bread and in the modified bread had no impact on the shape of the curve. On the other hand, the type of bread had a significant effect on the death kinetics of the bacterial population, which was prolonged from 67.46 to 80.53 at 0.4 g/l and from 70.28 to 93.96 at 0.8 g/l when using the bread prepared with flour whose seeds were treated with the method described above.

The effect of the bread prepared with flour whose seeds were treated with the previously described method, on the death kinetics, but not on the shape parameter, is a consequence of a probable reduction in mortality in the last part of the death curve, as suggested by the death kinetics of *Lactobacillus acidophilus* in saline solution after the addition both of the control bread and of the treated bread (0.8 g/l) shown in FIG. 11. The lines represent the best fit through Weibull's equation. A second test was carried out to determine whether the concentration of modified bread could cause or exercise a harmful effect both on *Lactobacillus acidophilus* and on *Bifidobacterium animalis*; the saline solution was added with the quantity used for the first experiment (0.8 g/l) and with a higher concentration (5.0 g/l) to simulate a local increase of the bread due to a slow transit in the intestine. The vital count was not influenced by the concentration of the digested bread and the death kinetics showed a similar trend to the one shown in FIG. 11.

Lastly, the saline solution was inoculated with a Gram-positive or Gram-negative pathogen (*Staphylococcus aureus* and *Salmonella Typhimurium*); the results for *Staphylococcus aureus* are shown in FIG. 12 which shows the vital counts in saline solution with the addition of the control bread or of the treated bread (0.2, 0.4 or 0.8 g/l). The mean values±standard deviation. The symbols "*" and "**" identify the significant differences (one-way ANOVA and Tukey's test).

A significant difference was observed for the sample with the addition of 0.8 g/l of bread prepared with flour whose seeds were treated according to the described method, which showed a lower vital count rate by 1-log compared to the sample to which the control bread was added. In the presence of *Salmonella* sp. a reduction of 3-log was observed in the same sample after 7 days, while the control bread determined a reduction of 1-log (FIG. 13).

Example 3

Study on the Therapeutic Effect in the Restoration of the Balance of the Intestinal Flora of the Celiac Patient in Model Systems That Simulate the Distal Part of the Colon An assessment was made of both the control bread and of the bread prepared with flour whose seeds were treated according to the method of the present invention, in the batch fermentation cultures (model systems with controlled pH that simulate the distal part of the colon that allow to study the effect of single compounds or of fibers).

The fecal samples were obtained from three healthy human volunteers (two males, one female, aged between 30 and 38 years; BMI: 18.5-25) exempt from known metabolic and gastrointestinal diseases (e.g., diabetes, ulcerative colitis, Crohn's disease, irritable bowel syndrome, peptic ulcer and cancer). All healthy donors were administered a standard questionnaire to collect information about health condition, drug use, clinical anamnesis, and the life style before the donor was asked to provide a fecal sample. For celiac donors (two females, one male, aged between 30 and 38; BMI: 18.5-25), a written informed consent was obtained in each case and the study was approved by the Research Ethics Committee of the University of Reading, UK (UREC 15/20: donated fecal sample collection center for the in vitro model systems of the human colon). All fecal samples collected from healthy and celiac donors were collected on site, preserved in an anaerobic cabinet (10% $H_2$-10% $CO_2$-80% $N_2$) and used no later than 15 minutes after collection. The samples were diluted 1:10 (w/v) in an anaerobic PBS solution (0.1 M solution of phosphate buffer, pH 7.4) and homogenized for 2 minutes. The containers for the fermentation of cultures in batch culture (280 ml) previously sterilized were filled with 45 ml of a model complex growth medium of the colon (Tejero-Sarinena S., et al., 2012). Thereafter, the containers were connected to a bath of circulating water at 37° C. and the $N_2$ gas lacking $O_2$ was injected to make them anaerobic before inoculation. The pH was buffered to 6.7 and 6.9 using a pH-meter with NaOH or HCl solutions (Electrolab260; Electrolab Ltd, Tewkesbury, United Kingdom). To the culture medium were then added 5 ml of fecal homogenate, prepared as described above, and 1 ml of digested bread.

For each donor, 3 different containers were prepared:
negative control (in which the digested bread was not added) called A for the healthy subjects and D for the celiac subjects;
container with the addition of control bread called B for the healthy subjects and E for the celiac subjects;
container with the addition of bread prepared with flour whose seeds were treated with the method described above called C for the healthy subjects and F for the celiac subjects.

The batch cultures were analyzed for 48 hours, drawing at the time of inoculation and after 6, 24 and 48 hours of time the samples necessary for the assessment of the microbiota through fluorescence in situ hybridization (FISH) and the determination of short chain fatty acids (SCFA) using high performance liquid chromatography (HPLC). FIGS. 14, 15 and 16 show the results of the analyses of the main components relating to the results of the SCFA and FISH after 6, 24 and 48 hours of fermentation.

The results obtained from the FISH and SCFA experiments were standardized as increase/decrease referred to t0 (inoculation) of the negative control, to exclude the variability due to the type of donor; therefore, the results show the modification of the system with respect to the start of the experiment and should be read as the increase (positive value) or decrease (negative values) of the microbial population or of the products of microbial metabolism. The increase/decrease is referred to the inoculation of the negative control (log cells/ml).

In addition, each parameter was analyzed through the ANOVA test to identify the significant differences; use of the approach for homogeneous groups was applied as an additional instrument to establish a possible trend over time. Table 3 below shows the results of the one-way ANOVA test for homogeneous groups on the FISH data of bifidobacteria after 6, 24 and 48 hours of fermentation.

TABLE 3

| Sample | FISH | Homogeneous groups | | |
|---|---|---|---|---|
| | | I | II | III |
| 6 hours | | | | |
| E | 0.147100 | **** | | |
| F | 0.264242 | **** | | |
| D | 0.489640 | **** | | |
| B | 0.604836 | **** | | |
| A | 0.632162 | **** | | |
| C | 0.700706 | **** | | |
| 24 hours | | | | |
| E | 0.371967 | **** | | |
| F | 0.490137 | **** | | |
| D | 0.507300 | **** | | |
| A | 0.716912 | **** | | |
| B | 0.734684 | **** | | |
| C | 0.909206 | **** | | |
| 48 hours | | | | |
| E | 0.273558 | | | **** |
| A | 0.654479 | **** | | |
| F | 0.681301 | **** | **** | |
| D | 0.707120 | **** | **** | |
| B | 0.715355 | **** | **** | |
| C | 0.925907 | | | **** |

Samples:
A, negative control healthy donors;
B, healthy donors + control bread;
C, healthy donors + modified bread;
D, negative controls celiac donors;
E, celiac donors + control bread;
F, celiac donors + modified bread The differences between the samples were not significant either after 6 hours, or after 24 hours. Instead, after 48 hours two statistical groups were observed: the first group consisted only of sample E (celiac donor with control bread) and the second group consisted of all other samples.

Sample E did not exhibit any significant increase in the population of bifidobacteria (increase 0.27-log cells/ml), probably due to a negative effect exercised by the bread on the microflora, while an increase from 0.7 to 0.9 log cells/ml occurred in the other samples. The interesting data resided, in fact, in the inclusion of the sample F with the samples of the healthy subject, suggesting a beneficial effect of the bread prepared with flour whose seeds had been treated with the method described above, able to restore a normal trend in the bifidobacteria population.

Tables 4 and 5 show the results of the one-way ANOVA tests for homogeneous groups on the FISH data relating to the bacterial groups Erec482 (Franks A. H. et al., 1998), Bac303 (Manz W. et al., 1996) after 6, 24 and 48 hours of fermentation (log cells/ml). The bacterial groups were identified using synthetic oligonucleotide probes intended for specific regions of 16S RNA (Langendijk P. S. et al., 1995) marked with the fluorescent dye Cy3 as reported in probeBase (http://www.microbial-ecology.net/probebase).

TABLE 4

| Sample | FISH | Homogeneous groups | | |
|---|---|---|---|---|
| | | I | II | III |
| 6 hours | | | | |
| B | 0.001945 | **** | | |
| A | 0.087913 | **** | | |
| C | 0.130655 | **** | | |

TABLE 4-continued

| Sample | FISH | Homogeneous groups | | |
|---|---|---|---|---|
| | | I | II | III |
| E | 0.159812 | **** | | |
| D | 0.370365 | **** | | |
| F | 0.382277 | **** | | |
| 24 hours | | | | |
| F | −0.065175 | | **** | |
| A | 0.077214 | **** | **** | |
| E | 0.169113 | **** | **** | |
| C | 0.286015 | **** | **** | |
| D | 0.443906 | **** | | |
| B | 0.481756 | **** | | |
| 48 hours | | | | |
| D | −0.017101 | **** | | |
| C | 0.051435 | **** | **** | |
| F | 0.064366 | **** | **** | **** |
| A | 0.150569 | **** | **** | **** |
| E | 0.223303 | | **** | **** |
| B | 0.267762 | | | **** |

Samples:
A, negative control healthy donors;
B, healthy donors + control bread;
C, healthy donors + modified bread;
D, negative controls celiac donors;
E, celiac donors + control bread;
F, celiac donors + modified bread.

TABLE 5

| Sample | FISH | Homogeneous groups | | | |
|---|---|---|---|---|---|
| | | I | II | III | IV |
| 6 hour | | | | | |
| A | −0.094164 | **** | | | |
| D | −0.043412 | **** | | | |
| E | 0.080924 | **** | | | |
| B | 0.106672 | **** | | | |
| C | 0.133569 | **** | | | |
| F | 0.176720 | **** | | | |
| 24 hours | | | | | |
| D | −0.189282 | **** | | | |
| E | −0.172388 | **** | | | |
| F | 0.028873 | **** | **** | | |
| A | 0.414786 | | **** | **** | |
| B | 0.433302 | | **** | **** | |
| C | 0.636738 | | | **** | |
| 48 hours | | | | | |
| B | −0.330564 | **** | | | |
| F | −0.313381 | **** | **** | | |
| E | −0.307379 | **** | **** | | |
| D | −0.193349 | | **** | **** | |
| C | −0.110862 | | | **** | **** |
| A | −0.034976 | | | | **** |

Samples:
A, negative control healthy donors;
B, healthy donors + control bread;
C, healthy donors + modified bread;
D, negative controls celiac donors;
E, celiac donors + control bread;
F, celiac donors + modified bread.

The statistical analysis highlighted a continuous distribution of the samples, with 2-4 superposed homogeneous groups, depending on time and on the type of microorganisms. The statistical distribution of the samples changed over time; however, the increase/decrease in the vital count (-0-33-0.26 log cells/ml) were of moderate size in absolute values. The effects of the addition of bread on the bacterial groups Chis150 (Franks A. H. et al., 1998) is shown in Table 6 below.

TABLE 6

| Sample | FISH | Homogeneous groups | | |
|---|---|---|---|---|
| | | I | II | III |
| 6 hours | | | | |
| B | −0.266858 | **** | | |
| A | −0.180315 | **** | | |
| C | −0.103523 | **** | **** | |
| D | 0.153936 | | **** | **** |
| F | 0.171644 | | **** | **** |
| E | 0.316956 | | | **** |
| 24 ore | | | | |
| C | −0.162934 | **** | | |
| F | −0.120933 | **** | | |
| A | −0.083551 | **** | | |
| B | −0.030945 | **** | | |
| E | 0.072539 | **** | | |
| D | 0.096110 | **** | | |
| 48 ore | | | | |
| A | −0.305986 | **** | | |
| C | −0.234457 | **** | | |
| B | 0.060428 | **** | | |
| D | 0.166901 | **** | | |
| F | 0.190838 | **** | | |
| E | 0.216414 | **** | | |

Samples:
A, negative control healthy donors;
B, healthy donors + control bread;
C, healthy donors + modified bread;
D, negative controls celiac donors;
E, celiac donors + control bread;
F, celiac donors + modified bread.

After 6 hours, a continuous distribution of the samples was observed with 2 well defined groups ($1^{st}$ group with the A and B samples; $2^{nd}$ group containing the sample E) and an intermediate class (samples C, D, F). Lastly, the sample E (celiac donor with control bread) was not statistically different from the samples D and F (negative control and celiac donor with "modified" bread) also statistically different from the samples of healthy donors. However, in the samples F and D a statistical shift towards the sample C was observed. This change was not observed after 24 and 48 hours. The lactic bacteria exhibited a characteristic trend over time, as shown in Table 7 below, which illustrates the results of the one-way ANOVA test for homogeneous groups on the FISH data of Lab 158 after 6, 24 and 48 hours of fermentation (log cells/ml).

TABLE 7

| Sample | FISH | Homogeneous groups | | |
|---|---|---|---|---|
| | | I | II | III |
| 6 hours | | | | |
| F | −0.639714 | | **** | |
| E | −0.565338 | | **** | |
| D | −0.327822 | **** | **** | |
| C | −0.122414 | **** | | |
| A | 0.001010 | **** | | |
| B | 0.038547 | **** | | |
| 24 hours | | | | |
| E | −0.591904 | | **** | |
| F | 0.014006 | **** | | |

TABLE 7-continued

| Sample | FISH | Homogeneous groups | | |
| --- | --- | --- | --- | --- |
| | | I | II | III |
| D | 0.015039 | **** | | |
| A | 0.165791 | **** | | |
| C | 0.267343 | **** | | |
| B | 0.288811 | **** | | |
| 48 hours | | | | |
| E | −0.526397 | | | **** |
| D | −0.289074 | **** | | **** |
| F | −0.022714 | **** | **** | **** |
| A | 0.135032 | **** | **** | |
| B | 0.188054 | **** | **** | |
| C | 0.304061 | | **** | |

Samples:
A, negative control healthy donors;
B, healthy donors + control bread;
C, healthy donors + modified bread;
D, negative controls celiac donors;
E, celiac donors + control bread;
F, celiac donors + modified bread.

After 6 hours of fermentation, a decrease was observed in the lactic population in the samples E and F (0.57-0.64 log cells/ml). After 24 hours, this negative trend was observed in the sample E, but not in the sample F, in which the lactic population increased and showed a similar trend to that of the healthy subjects, suggesting an interesting and beneficial effect of the bread prepared with flour whose gluten proteins were modified.

After 48 hours, their distribution was continuous; the sample F, in particular, was positioned in an intermediate group between the healthy subjects and the sample E.

The statistical results for the bacterial groups Eu (Eub338 I, Eub338 II, Eub338 III (used together) (Daims H. et al., 1999), showed a constant distribution, without significant differences between the different samples.

Table 8 below shows the results of the one-way ANOVA test for homogeneous groups on the FISH data of Eu after 6, 24 and 48 hours of fermentation (log cells/ml).

TABLE 8

| Sample | FISH | Homogeneous groups | |
| --- | --- | --- | --- |
| | | I | II |
| 6 hours | | | |
| B | −0.132923 | **** | |
| A | −0.061032 | **** | |
| C | 0.056311 | **** | |
| F | 0.238798 | **** | |
| D | 0.336604 | **** | |
| E | 0.435467 | **** | |
| 24 hours | | | |
| A | 0.274960 | | **** |
| B | 0.488056 | **** | **** |
| C | 0.496600 | **** | **** |
| F | 0.599021 | **** | **** |
| D | 0.720836 | **** | |
| E | 0.825880 | **** | |
| 48 hours | | | |
| C | −0.197966 | | **** |
| B | −0.005315 | **** | **** |
| A | 0.102244 | **** | **** |

TABLE 8-continued

| Sample | FISH | Homogeneous groups | |
| --- | --- | --- | --- |
| | | I | II |
| D | 0.265949 | **** | **** |
| F | 0.345989 | **** | |
| E | 0.434101 | **** | |

Samples:
A, negative control healthy donors;
B, healthy donors + control bread;
C, healthy donors + modified bread;
D, negative controls celiac donors;
E, celiac donors + control bread;
F, celiac donors + modified bread.

The same approach was used to analyses the results of the SCFA (short chain fatty acids). SCFAs generally showed a discrete distribution of the results with well-defined statistical groups and significant differences. The results are illustrated in Tables 9, 10 and 11 below.

Table 9 shows the one-way ANOVA test for homogeneous groups of butyric acid after 24 and 48 hours; the mean increase compared to the negative control is indicated (mM).

TABLE 9

| Sample | SCFA | Homogeneous groups | | | | | |
| --- | --- | --- | --- | --- | --- | --- | --- |
| | | I | II | III | IV | V | VI |
| 24 hours | | | | | | | |
| C | 43.3736 | **** | | | | | |
| A | 45.3854 | | **** | | | | |
| D | 52.3644 | **** | | | | | |
| F | 52.3767 | **** | | | | | |
| E | 62.2977 | | | | **** | | |
| B | 174.0981 | | | | | **** | |
| 48 hours | | | | | | | |
| A | 43.8577 | **** | | | | | |
| F | 52.9641 | | **** | | | | |
| E | 57.6583 | | | **** | | | |
| D | 61.8410 | | | | **** | | |
| C | 62.4645 | | | | | **** | |
| B | 258.4700 | | | | | | **** |

Samples: A, negative control healthy donors; B, healthy donors + control bread; C, healthy donors + modified bread; D, negative controls celiac donors; E, celiac donors + control bread; F, celiac donors + modified bread.

Table 10 shows the one-way ANOVA test for homogeneous groups of propionic acid after 24 and 48 hours; the mean increase compared to the negative control is indicated (mM).

With regard to the propionic acid, the increase was small in the samples of healthy donors (both after 24 hours and 48 hours), while its concentration increased by 23-37 mM in the samples of the celiac donors.

TABLE 10

| Sample | SCFA | Homogeneous groups | | | | | |
| --- | --- | --- | --- | --- | --- | --- | --- |
| | | I | II | III | IV | V | VI |
| 24 hours | | | | | | | |
| B | −4.30662 | **** | | | | | |
| A | −0.75728 | | **** | | | | |
| C | 0.96521 | | | **** | | | |
| D | 23.15887 | | | | **** | | |
| E | 31.18544 | | | | | **** | |
| F | 32.70900 | | | | | | **** |

TABLE 10-continued

| | | Homogeneous groups | | | | | |
|---|---|---|---|---|---|---|---|
| Sample | SCFA | I | II | III | IV | V | VI |
| 48 hours | | | | | | | |
| A | 0.39286 | **** | | | | | |
| B | 1.71661 | | **** | | | | |
| C | 4.68863 | | | **** | | | |
| D | 22.58833 | | | | **** | | |
| F | 37.13872 | | | | | **** | |
| E | 37.45659 | | | | | | **** |

Samples: A, negative control healthy donors; B, healthy donors + control bread; C, healthy donors + modified bread; D, negative controls celiac donors; E, celiac donors + control bread; F, celiac donors + modified bread.

Table 11 shows the one-way ANOVA test for homogeneous groups of butyric acid after 24 and 48 hours; the mean increase compared to the negative control is indicated (mM).

TABLE 11

| | | Homogeneous groups | | | | | |
|---|---|---|---|---|---|---|---|
| Sample | SCFA | I | II | III | IV | V | VI |
| 24 hours | | | | | | | |
| C | −3.63255 | **** | | | | | |
| B | −0.38556 | | **** | | | | |
| A | 2.43478 | | | **** | | | |
| F | 4.07283 | | | | **** | | |
| E | 7.59356 | | | | | **** | |
| D | 17.42258 | | | | | | **** |
| 48 hours | | | | | | | |
| A | 2.24822 | **** | | | | | |
| B | 4.01809 | | **** | | | | |
| F | 4.27836 | | | **** | | | |
| C | 6.58688 | | | | **** | | |
| E | 10.66568 | | | | | **** | |
| D | 15.03661 | | | | | | **** |

Samples: A, negative control healthy donors; B, healthy donors + control bread; C, healthy donors + modified bread; D, negative controls celiac donors; E, celiac donors + control bread; F, celiac donors + modified bread.

After 24 hours, butyric acid increased by 17 mM in the negative control D, which recorded the greatest increase, followed by the other two samples of the celiac donors (respectively E, 7.6 mM and F, 4.1 mM); the results after 48 hours showed an interesting trend, inasmuch as the sample F showed a similar profile to the samples of the healthy donors, with a net increase of 4.28 mM in butyric acid. FIGS. 15, 16 and 17 show the study of the global differences relating to the batch cultures coming from the healthy and celiac donors through an analysis of the main components; the results of the SCFA and of the FISH were all used as inputs; for every time of analysis, a different analysis was carried out.

After 6 hours, two statistical groups could be identified in the multifactorial space: the first one consisted of the samples from the healthy subjects (A, B and C) and the second one of the samples E and F.

The negative control of the celiac donors (sample D) was situated in a different region of the space (FIG. 14).

After 24 hours, the distribution of the space changed drastically (FIG. 15); the group coming from the healthy donors divided into two sub-groups, because the sample B shifted to a different region of the space, but the interesting result involved the sample F which shifted from the factorial region occupied by the samples from the celiac subjects and moved towards the region of the samples of the healthy subjects A and C. A similar effect was observed after 48 hours (FIG. 16).

Example 4

Study on the Therapeutic Effect in the Improvement of the Composition and Metabolism of Gut Flora in Healthy Patients and Celiacs in Model Systems Simulating the Proximal, Transverse and Distal Part of the Colon The effect of control and modified bread whose grains have been treated according to the gluten epitopes detoxification method of the invention has been evaluated, in a three-steps continuos fermentation culture simulating the proximal, transverse and distal part of human colon (vessel 1, 2 and 3, respectively).

Foecal samples were obtained from two healthy and two celiacs volunteers (men and women of age between 30 and 50 yrs; BMI: 18, 5-25) without known metabolic or gastrointestinal diseases (such as diabetes, ulcerative colitis, Crohn's disease, irritable colon syndrome, peptic ulcer and cancer) who did not take any probiotic or prebiotic supplement, and antibiotics 6 months before the graft of the foecal sample.

A standard questionnaire has been submitted to the healthy donors to collect information on healthy status, drug consumption, case history, and life style before requiring the foecal sample. The study has been approved by The University of Roehampton Research Ethics Committee (UREC 15/20).

Foecal samples have been stored in anaerobic jar (AnaeroJar™ 2.5 L, Oxoid Ltd) including a gas regeneration kit (AnaeroGen™, Oxoid) in order to reproduce anaerobic conditions inside the room. A 20 g aliquot of each sample has been diluted in 100 ml of anaerobic PBS solution (0.1 M phosphate solution, pH 7.4, w/w) and homogenized for 2 minutes (Stomacher 400, Seward, West Sussex, UK). Samples have been added to the anaerobic fermenters within 15 minutes from their preparation. Physical-chemical colon conditions have been repeated in a three-step continuous system made by three glass fermenters with increasing volume and serially connected. For the first time in this study a small scale version of the system validated by Macfarlane et al. (1998) has been used, wherein the proximal part of the colon was represented by vessel 1 (V1, 80 ml), the transverse part of the colon by vessel 2 (V2, 100 ml), and the distal part by vessel 3 (V3, 120 ml) inoculated with 20% (w/v) of foecal homogenate of healthy and celiacs volunteers in a growth medium. The growth medium contained the following ingredients: starch, 5 g/l; mucin, 4 g/l; casein, 3 g/l; peptone water, 5 g/l; tryptone water, 5 g/l; biliary salts, 0.4 g/L; yeast extract, 4.5 g/l; $FeSO_4$, 0.005 g/l; NaCl, 4.5 g/l; KCl, 4.5 g/l; $KH_2PO_4$, 0.5 g/l; $MgSO_4 \times 7H_2O$, 1.25 g/l; $CaCl_2 \times 6H_2O$, 0.15 g/l; $NaHCO_3$, 1.5 g/l; Tween 80, 1 mL; hemin, 0.05 g/l; and cysteine HCl, 0.8 g/l.

Following inoculum, bacterial population have been stabilized as batch culture for 24 hrs. After 24 hrs (T0), the model system runs for 8 complete volume rounds to enable the achievement of the steady state (SS1) (verified through the stabilization of SCFA profiles (+/−5%).

Keeping in mind the working volume (300 ml) and retention time (48 hrs, flow rate 6.25 ml/hr) of the model system, in vitro digested control or modified bread (3.75 ml) in suitable conditions according to the procedure disclosed by Maccaferri S. et al. (2012) have been daily added in vessel V1. The bread has been added to the system for further 8 complete volume rounds until the achievement of the steady state 2 (SS2).

4.5 mL aliquots have been removed and analyzed at SS1 (day $T_0$) and SS2 (day $T_{30}$).

Changes in the bacterial compositions of the model system simulating the three parts of the colon have been evaluated through FISH analysis (FIGS. 17 and 18) whilst changes of the microflora metabolism have been evaluated by the determination of short chain fatty acids (SCFA) (FIGS. 19 and 20) by high performance liquid chromatography (HPLC).

Results of the effect of control bread on healthy volunteers depicted in FIG. 17 showed a meaningful decrease in the number of Lactobacillus/Enterococcus spp. (detected by the probe Lab158) (vessel V1 and V2), Bacteroides-Prevotella group (V2) (detected by the probe Bac303) and Clostridium clusters XIVa+b (V1) (detected by the probe Erec482).

A total bacteria decrease trend has been observed in all the steps of the model system also if such differences have not been resulted as significant. Then, the control bread had not positive impact on the modulation and composition of foecal microflora.

Instead, the administration of the bread treated according to the method of the invention, led to a significant increase of bifidobacteria (detected by the probe Bif164) both in celiacs and healthy volunteers.

Particularly, in celiacs subjects a significant increase of bifidobacteria from 8.42 to 8.90 Log CFU/ml has been observed (P<0.05) in the second step of model system (vessel 2) and from 8.60 to 9.20 Log CFU/ml (P<0.05) in vessel 3, respectively.

In healthy subjects, a significant increase in the number of bifidobacteria from 7.90 to 8.40 Log CFU/ml (P<0.05) has been observed in vessel 3 (FIG. 18).

Furthermore, in celiacs volunteers it has been observed a significant increase of the Clostridium cluster from 8.85 to 9.50 Log CFU/ml (P<0.05); from 9.1 to 9.60 Log CFU/ml (P<0.01) and from 9 to 9.50 Log CFU/ml (P<0.05) in all vessels, respectively.

The general trend of the enhancement in all the bacterial groups and in all vessels has been detected in both healthy and celiacs subjects, without any significant differences.

SCFAs have been measured by HPLC at SS1 and SS2 in all the three different vessels of the model system (FIGS. 19 and 20). The administration of control bread induces a significant decrease of the acetate (V1 and V2) and propionate (V1), and an increase of butyrate in all vessels (FIG. 19).

In healthy subjects, the fermentation of the modified bread led to a significant production of acetate from 28.80 to 22.10 mM (P<0.01) in V1, from 44.40 to 56.94 mM (P<0.01) in V2 ad from 46 to 76.50 mM (P<0.001) in V3, respectively. Furthermore, a significant increase of propionate concentration from 70.46 to 89.81 mM (P<0.05) in V1, and of butyrate concentration from 40.35 to 77.09 mM (P<0.05) in V3, has been observed. In celiacs volunteers, a significant increase of propionate levels from 45.10 to 69.20 mM (P<0.01) in vessel 1 and from 50.80 to 70.20 mM (P<0.05) in vessel 2, has been observed, respectively.

Moreover, a significant increase of acetate concentration in vessel 1 from 41.20 to 89 mM (P<0.01) has been detected (FIG. 20).

From the results, it is inferred that in vitro fermentation of the modified bread induced a modulation of the colon microbiota with an increase of the acetate and propionate concentration that, has not been observed with the control bread in healthy subjects.

The most known metabolic pathway in gastrointestinal bacteria for the production of acetate and propionate concerns the polysaccharides metabolism.

Acetate production is mainly achieved through the metabolic pathway of fructose-6-phosphate phosphoketolase by bifidobacteria, and the main production of such acid is strictly correlated with the bacteria enhancement (Miller T. L. et al., 1996).

According to Hosseini E. et al. (2011), propionate may be produced by fermentable carbohydrates through two metabolic pathways. The first one foreses succinate decarboxylation in the presence of Bacteroides fragilis and Propioni bacterium spp., while the second one foresees the metabolic pathway of acrylate, wherein pyruvate is reduced to lactate by lactate dehydrogenase in the presence of some clusters of Clostridi. During the fermentation of the modified bread a significant increase of bifidobacteria, Bacteroides and E. rectale groups has been observed.

Modified bread showed a positive modulation of the composition of the microbiota as well as an increase of SCFAs concentration in both healthy and celiac donors.

After, the fermentation of the modified bread creates a positive modulation in terms of bifidogenic effect in both healthy and celiac subjects and in terms of growth number of Clostridium XIVa+b in celiacs subjects.

Although in healthy subjects acetic and propionic acid levels were reduced in vessel 1, acetic acid levels were considerably increased in vessels V2 and V3, and butyric acid levels were increased in vessel V3. Furthermore, as for celiac subjects high concentrations of acetic and propionic acid in vessel V1, and of propionate in vessel V2 have been observed.

BIBLIOGRAPHY

Shuppan, D., Yunker, Y., Barisani, D. 2009. Gastroenterology, 137(6):1912-33.
Rossi, M. Schwartz, K. B. J. Leukoc. Biol. 87, 749-751 (2010).
Sánchez, E., Donat, E., Ribes-Koninckx, C., Fernández Murga, M. L. Sanz, Y. 2013. Appl. Environ. Microbiol. 79, 5472-5479.
Wacklin, P. et al.2013. Inflamm. Bowel Dis. 19, 934-941.
Collado, M. C., Donat, E., Ribes-Koninckx, C., Calabuig, M. & Sanz, Y. 2009. J. Clin. Pathol. 62, 264-269.
Collado, M., Donat, E., Ribes-Koninckx, C., Calabuig, M. & Sanz, Y. 2008. BMC Microbiol. 8, 232.
Di Cagno, R.et al. 2011.BMC Microbiol. 11, 219
De Palma, G. et al. 2010. BMC Microbiol. 10, 63.
Sanz, Y.et al. 2007. FEMS Immunol. Med. Microbiol. 51, 562-568.
Nadal, I., Donant, E., Ribes-Koninckx, C., Calabuig, M. & Sanz, Y. 2007. J. Med. Microbiol. 56, 1669-1674.
Schippa, S. et al. 2010. BMC Microbiol. 10, 175.
Wacklin, P. et al. 2014. Am. J. Gastroenterol. 109, 1933-1941.
Cenit, M. C.,Olivares, M., Codoner-Franch. P., Sanz, Y. 2015. Nutrients, 7, 6900-6923.
Smecuol, E.; Hwang, H. J.; Sugai, E.; Corso, L.; Cherñavsky, A. C.; Bellavite, F. P.; González, A.; Vodánovich, F.; Moreno, M. L.; Vazquez, H. 2013. J. Clin. Gastroenterol., 47, 139-147.
Olivares, M.; Castillejo, G.; Varea, V.; Sanz, Y. 2014. Br. J. Nutr., 112, 30-40.

Klemenak, M.; Dolinšek, J.; Langerholc, T.; Di Gioia, D. Dig. Dis. Sci., 7. 3454-3460.

Lamacchia C., Landriscina L., D'Agnello P. 2016. Food Chemistry, 197, 634-640.

WO 2014/053891

Noel T R, Parker R, Ring S G, Tatham A S. 1995. Int J Biol Macromol, 17:81

Micard, V., and Guilbert, S. 2000. International Journal of Biological Macromolecules, 27, 229-236.

Tosi, P., Gritsch, C. S., He, J., Shewry, P. R. 2011. Annals of Botany, 108, 23-25.

Lamacchia C., Di Luccia, A., Baiano, A., Gambacorta, G., La Gatta, B., Pati, S., La Notte, E. 2007. Journal of Cereal Science, 46, 58-63.

Gerrard, J. A. 2000. Trends in Food Science and Technology, 13, 391-399.

Tilley, K. A., Benjamin, R. E., Bagorogoza, K. E., Okoy-Kotber, B. M., Prakash, O., Kwen, H. 2001. 49 (5), 2627-2632.

Maccaferri S, Klinder A, Cacciatore S, Chitarrari R, Honda H, et al. 2012. Molecular Nutrition and Food Research 56, 1342-1352.

Tejero-Sarinena, S., Barlow, J., Costabile, A. Gibson, G. R. and Rowland, I. 2012 Anaerobe, vol. 18, no. 5, pp. 530-538.

Franks A H, Harmsen H J, Raangs G C, Jansen G J, Schut F, et al. 1998. Applied and Environmental Microbiology 64, 3336-3345.

Manz W, Amann R, Ludwig W, Vancanneyt M, Schleifer K H. 1996. Microbiology 142, 1097-1106.

Langendijk P S, Schut F, Jansen G J, Raangs G C, Kamphuis G R, et al. 1995. Applied Environmental Microbiology 61, 3069-3075.

Maccaferri S, Klinder A, Cacciatore S, Chitarrari R, Honda H, Luchinat C, Bertini I, Carnevali P, Gibson G R, Brigidi P, Costabile A. Mol Nutr Food Res 2012, 56:1342-52.

Macfarlane G T, Macfarlane S, Gibson G R. Microb Ecol 1998, 35:180-7.

Hosseini E, Grootaert C, Verstraete W, Wiele T V. Nutr Rev 2011, 69(5):245-58.

Miller T L, Wolin M J. Appl Environ Microbiol 1996, 62 (5):1589-92.

The invention claimed is:

1. A method of producing cereal grains containing gluten having detoxified gluten proteins, comprising:
hydrating cereal grains with water up to a humidity degree of the cereal grains between 15% and 18%;
treating the hydrated cereal grains by electromagnetic waves for a time and with a power to reach a first temperature of the cereal grains between 60° C. and 70° C.;
suspending the electromagnetic waves until the hydrated cereal grains reach a second temperature between 50° C. and 60° C. and a first humidity loss between 14% and 16%;
treating the hydrated cereal grains by electromagnetic waves for a time and with a power to reach a third temperature of the hydrated cereal grains between 80° C. and 90° C.;
suspending the electromagnetic waves until the hydrated cereal grains reach a fourth temperature between 70° C. and 80° C. and a second humidity loss between 40% and 44%;
treating the hydrated cereal grains by electromagnetic waves for a time and with a power to reach a fifth temperature of the hydrated cereal grains between 110° C. and 120° C.;
suspending the electromagnetic waves until the hydrated cereal grains reach a sixth temperature between 80° C. and 90° C. and a third humidity loss between 50% and 60%; and
cooling the hydrated cereal grains at room temperature to produce the cereal grains having detoxified gluten proteins.

2. The method of claim 1, wherein said electromagnetic waves are microwaves or infrared.

3. The method of claim 1, wherein when the electromagnetic waves are microwaves, the steps of treating the hydrated grains are carried out in a microwave oven.

4. The method of claim 1, further comprising milling the cereal grains containing gluten having detoxified gluten proteins to obtain detoxified flours or semolina.

5. The method of claim 4, further comprising extracting gluten from the detoxified flours or semolina with solvents.

6. The method of claim 1, wherein the cereal grains are selected from the group consisting of wheat, barley, orzo, rye and oat.

7. The method of claim 1, wherein the cereal grains containing gluten having detoxified gluten proteins have a level of toxic gluten epitopes reduced to a range between 0 and 20 ppm.

8. Cereal grains containing gluten having detoxified gluten proteins obtained by the method of claim 1, wherein the cereal grains have a level of toxic gluten epitopes reduced to a range between 0 and 20 ppm.

9. A food product comprising the cereal grains containing gluten having detoxified gluten proteins of claim 8, the food product selected from the group consisting of bread, pasta, bakery products, breakfast cereals, beer, ice-cream, dairy products, sauce, juice, baby foods, and salami.

10. A protective agent towards probiotic species, comprising the cereal grains containing gluten having detoxified gluten proteins of claim 8.

11. The protective agent of claim 10, wherein the probiotic species belong to the *Lactobacilli* genus.

12. The protective agent of claim 10, wherein the probiotic species belong to the species *Lactobacillus acidophilus*.

13. A thickening agent for the preparation of foodstuff, comprising the cereal grains containing gluten having detoxified gluten proteins of claim 8.

* * * * *